(12) United States Patent
Fattori et al.

(10) Patent No.: US 11,523,911 B2
(45) Date of Patent: Dec. 13, 2022

(54) GLENOID ADAPTER FOR SHOULDER JOINT PROSTHESIS

(71) Applicant: Limacorporate S.p.A., Villanova di San Daniele del Friuli (IT)

(72) Inventors: Andrea Fattori, Cividale del Friuli (IT); Simone Ursella, Majano (IT)

(73) Assignee: Limacorporate S.p.A., Villanova di San Daniele del Friuli (IT)

( * ) Notice: Subject to any disclaimer, the term of this patent is extended or adjusted under 35 U.S.C. 154(b) by 0 days.

(21) Appl. No.: 17/290,572

(22) PCT Filed: Jun. 12, 2020

(86) PCT No.: PCT/EP2020/066285
§ 371 (c)(1),
(2) Date: Apr. 30, 2021

(87) PCT Pub. No.: WO2020/249720
PCT Pub. Date: Dec. 17, 2020

(65) Prior Publication Data
US 2022/0151794 A1    May 19, 2022

(30) Foreign Application Priority Data

Jun. 14, 2019 (IT) .................. 102019000009015

(51) Int. Cl.
*A61F 2/40* (2006.01)
*A61F 2/30* (2006.01)
(52) U.S. Cl.
CPC ........ *A61F 2/4081* (2013.01); *A61F 2/30749* (2013.01); *A61F 2002/30332* (2013.01);
(Continued)

(58) Field of Classification Search
CPC .................. A61F 2/4081; A61F 2002/4085
See application file for complete search history.

(56) References Cited

U.S. PATENT DOCUMENTS 9,592,128 B2    3/2017  Phipps

FOREIGN PATENT DOCUMENTS

EP        1591084 A1    11/2005
EP        3270828 A1     1/2018
(Continued)

OTHER PUBLICATIONS

Written Opinion of the International Searching Authority issued in connection with PCT/EP2020/066285.
(Continued)

*Primary Examiner* — Brian A Dukert
(74) *Attorney, Agent, or Firm* — Akerman LLP

(57) ABSTRACT

The present invention relates to an improved glenoid adapter for shoulder prostheses, in particular for the conversion of an anatomic resurfacing prosthesis to a reverse shoulder prosthesis, comprising: •—at least one fixing projection (2) having an own axis (X) and being arranged to be fixed to the glenoid cavity (301) of the scapula (300) •—a flange (4) integral with said fixing projection (2); •—an attachment portion (3) integral with the flange (4) and extended in the direction opposite said fixing projection (2), as well as arranged to be coupled with an articular component (10) of reverse prosthesis provided with a convex articular surface (11), said attachment portion (3) having an own longitudinal axis (Y); both the fixing projection (2) and the attachment portion (3) have truncated-cone shape and that the axis of the attachment portion (Y) is misaligned with respect to the fixing projection axis (X); said flange (4) has a glenoid surface (4a) from which said fixing attachment (2) rises.

16 Claims, 20 Drawing Sheets

(52) U.S. Cl.
CPC ............... *A61F 2002/30507* (2013.01); *A61F 2002/4085* (2013.01)

(56) References Cited

FOREIGN PATENT DOCUMENTS

| | | | |
|---|---|---|---|
| WO | 2016/147163 | A1 | 9/2016 |
| WO | 2019/079104 | A2 | 4/2019 |

OTHER PUBLICATIONS

International Search Report issued in connection with PCT/EP2020/066285.

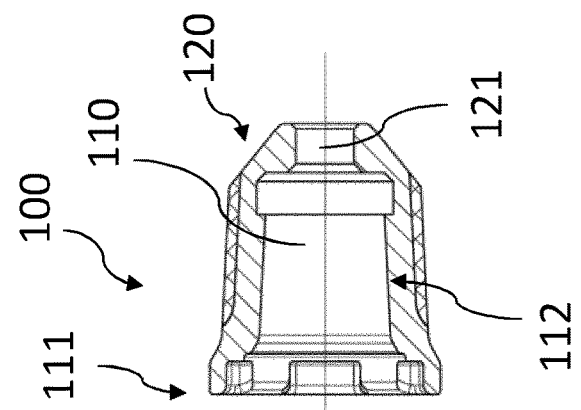
Fig. 10
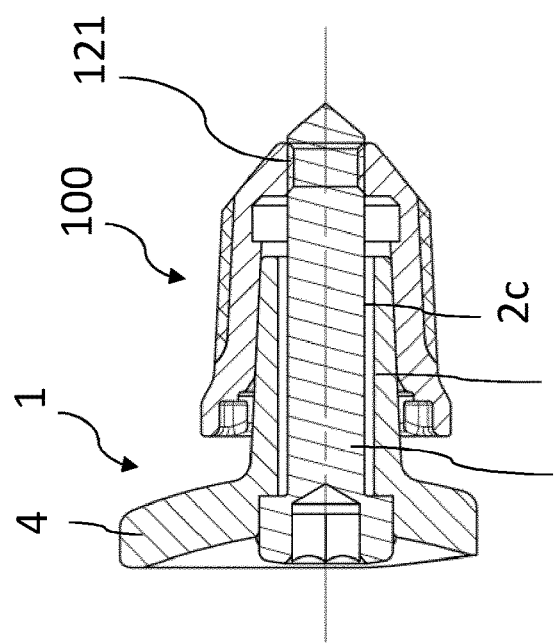
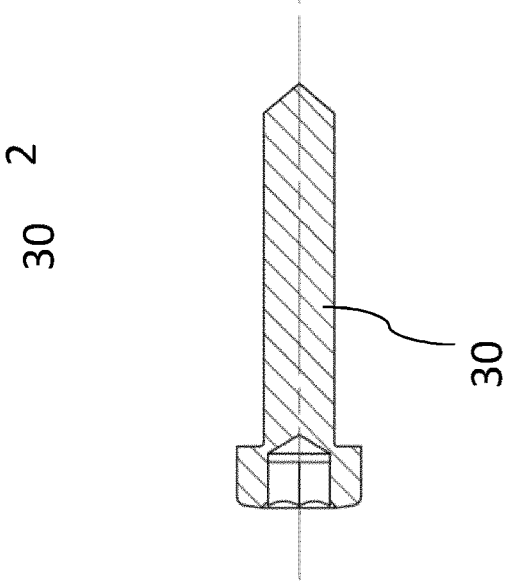
Fig. 11

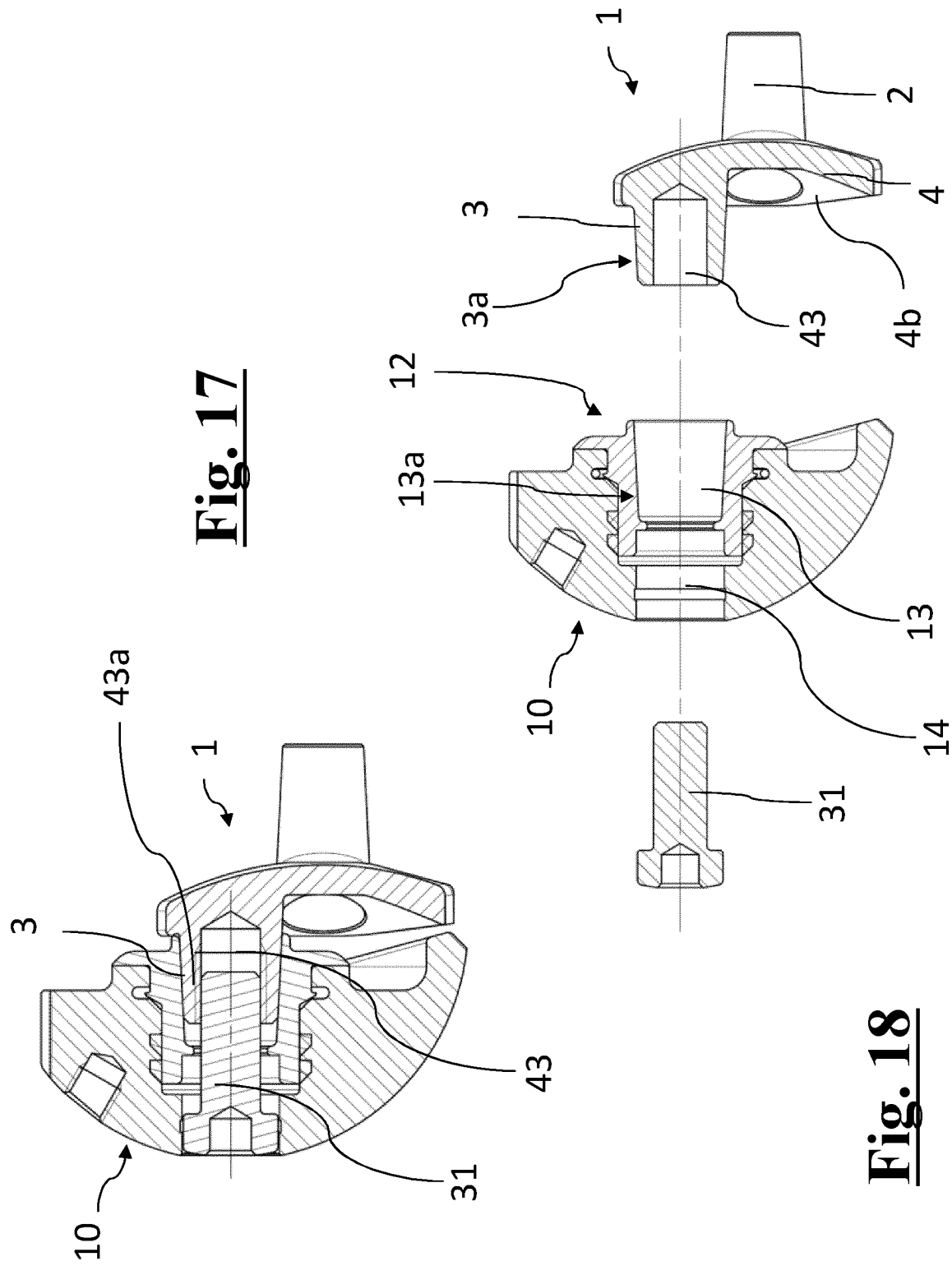

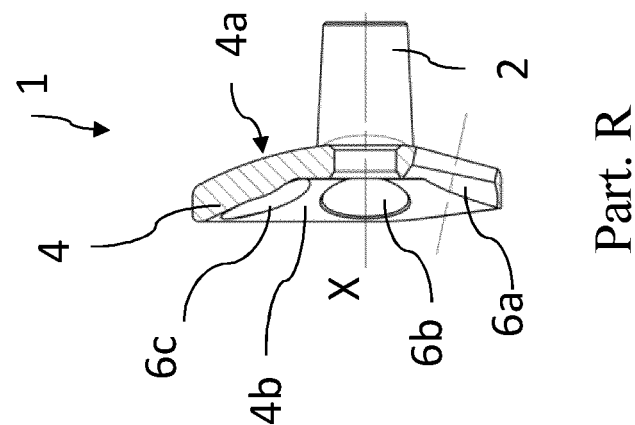
Part. R
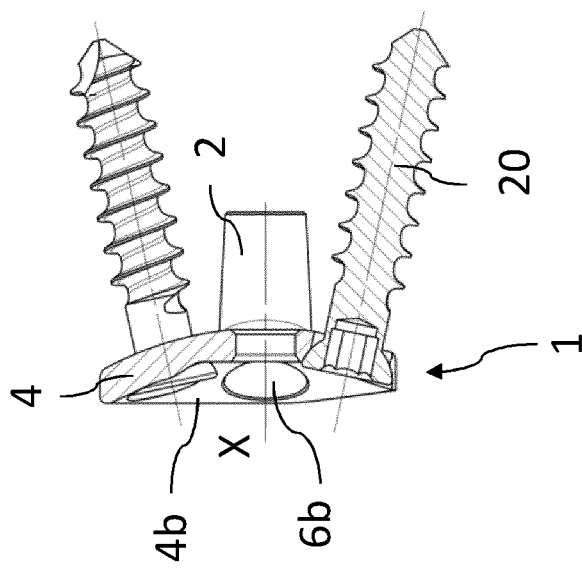
Fig. 25
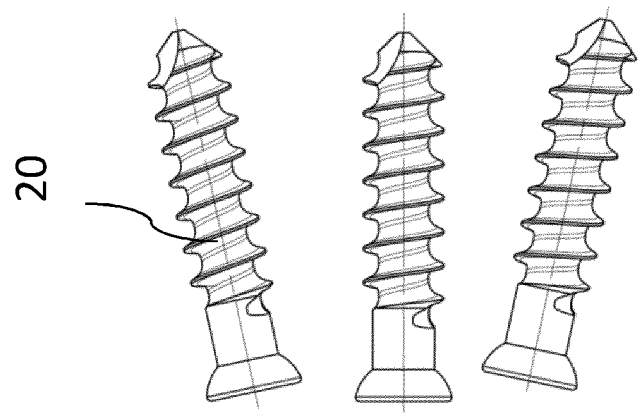
Fig. 26

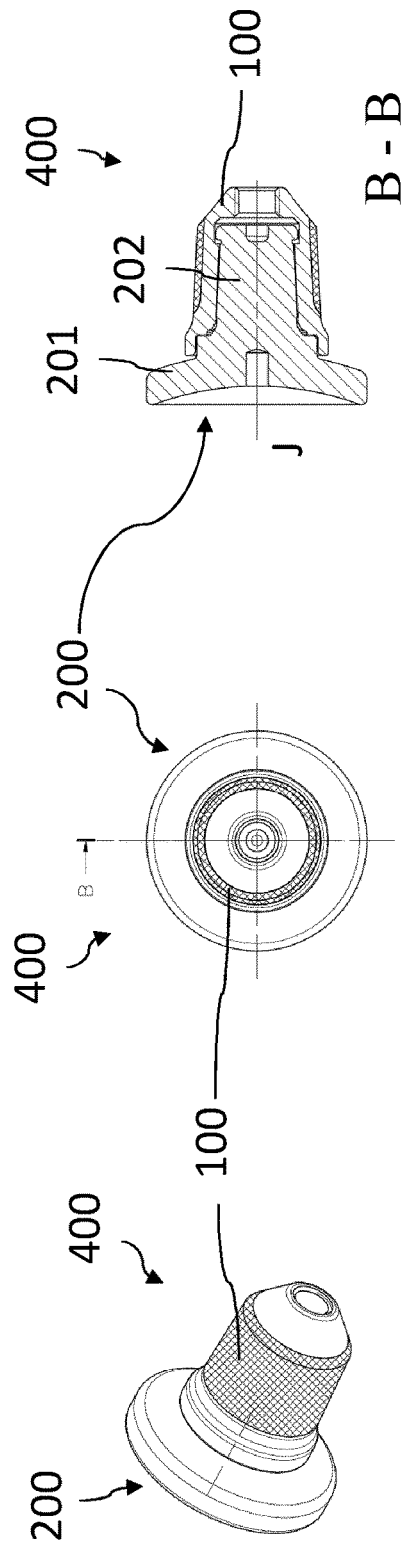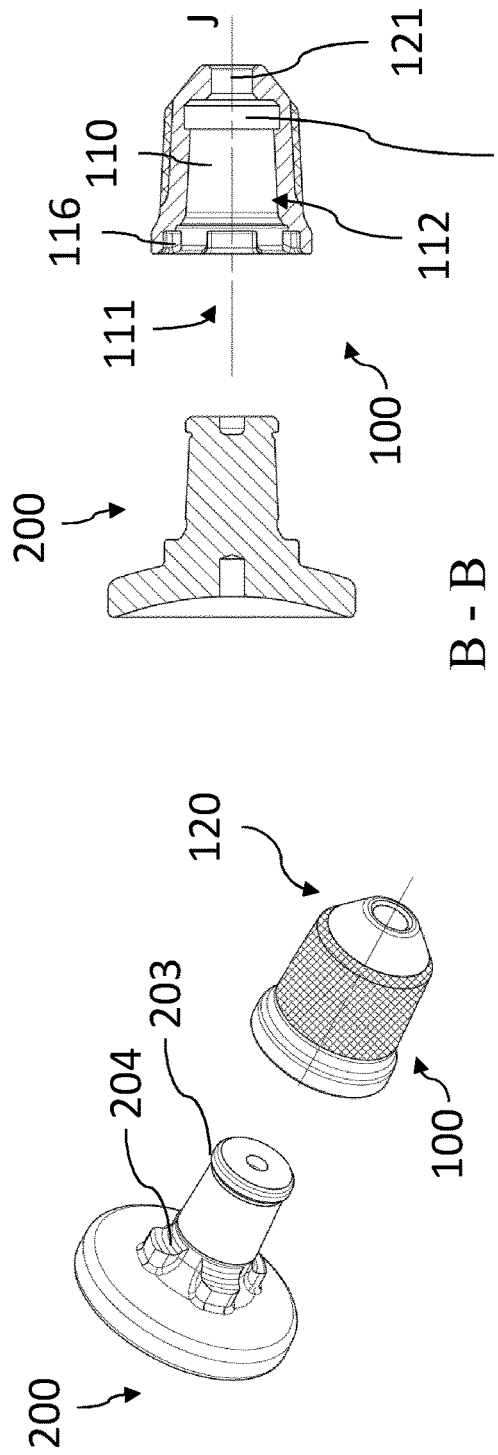

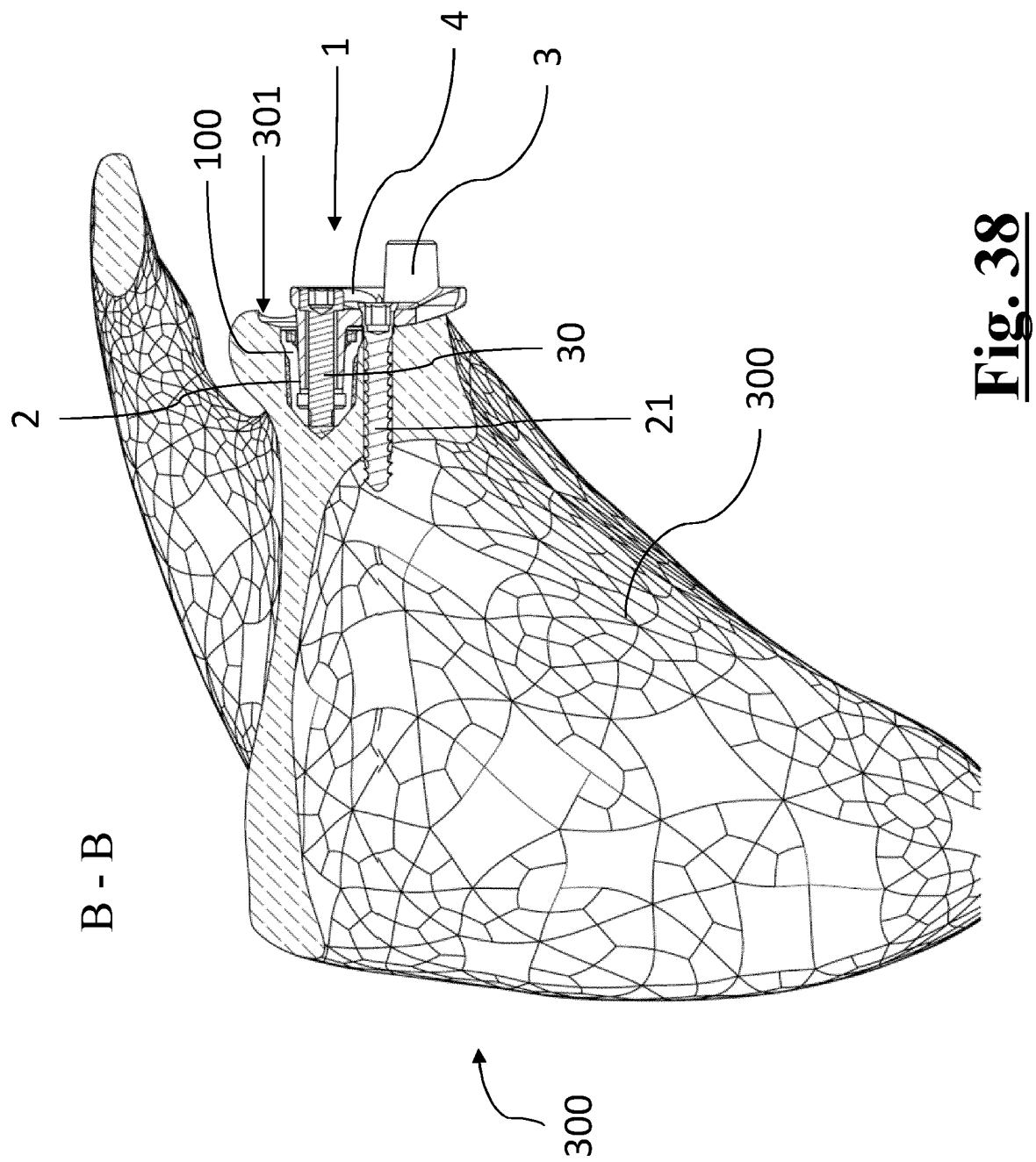

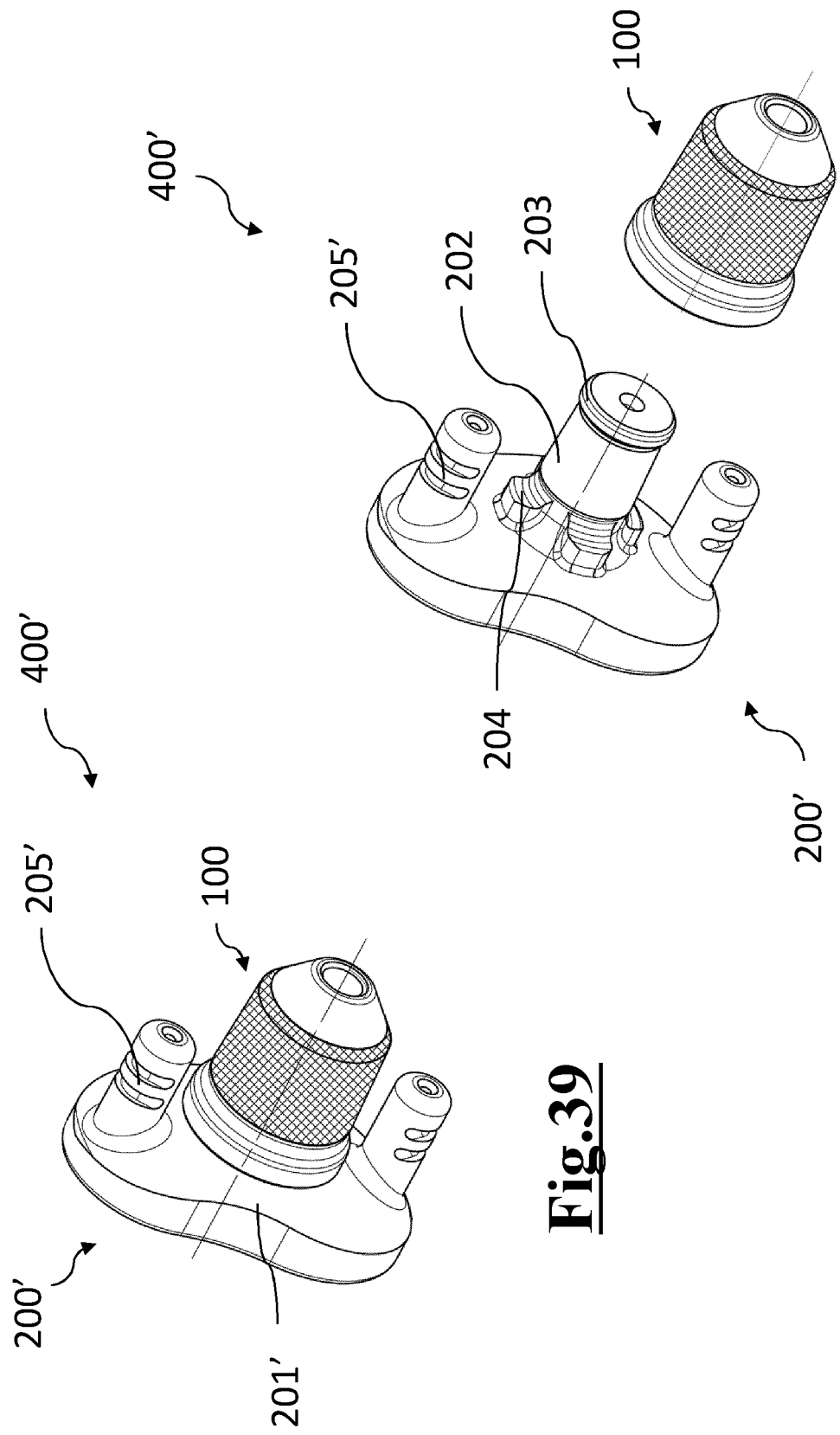

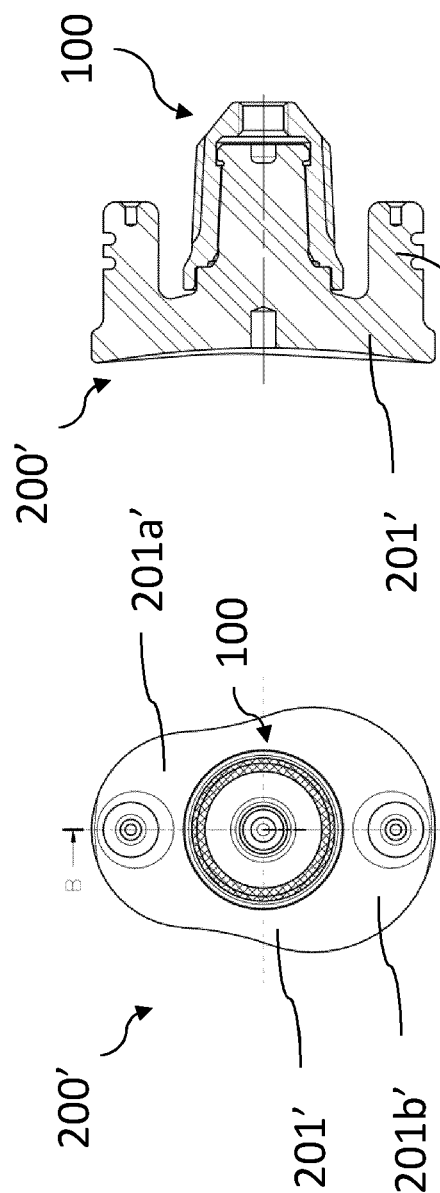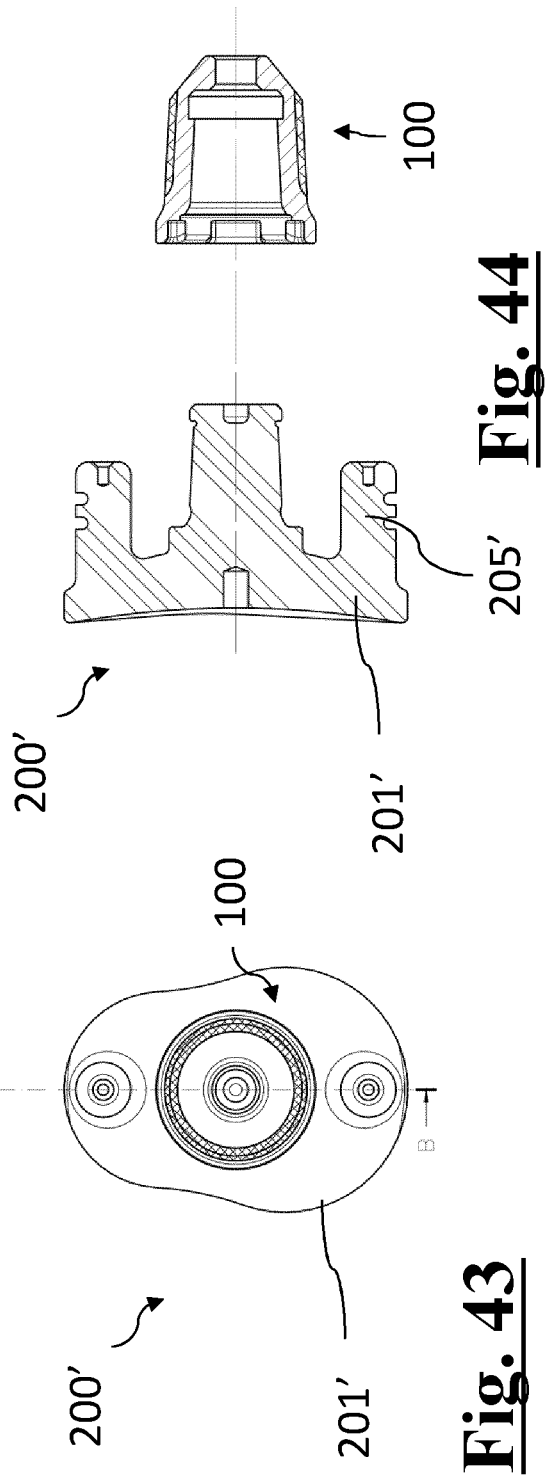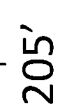

GLENOID ADAPTER FOR SHOULDER JOINT PROSTHESIS

CROSS-REFERENCE TO RELATED APPLICATIONS

This application is a national phase of PCT/EP2020/066285, filed Jun. 12, 2020, and claims priority to IT 102019000009015, filed Jun. 14, 2019, the entire contents of both of which are hereby incorporated by reference.

FIELD OF APPLICATION

The present invention relates to a glenoid adapter for implanting a convex articular component of reverse prosthesis.

The invention finds particular usefulness in the conversion of a so-called anatomic resurfacing prosthesis to a reverse prosthesis, in particular in the case when the anchor of the anatomic prosthesis has been inserted in a peripheral area of the glenoid cavity; the following description is made with reference to this specific field of application in order to simplify the exposition thereof.

The invention can be also employed to fix a convex component of reverse prosthesis to a glenoid cavity with lack of bone tissue on the central area, for example due to the removal of an anatomical prosthesis.

PRIOR ART

As it is well known, in the field of shoulder prostheses, the usage of so-called hybrid or convertible prostheses is already rather widespread which consist in modular prostheses made up of a plurality of elements which can be combined with each other to obtain a reverse or anatomical prosthesis and to possibly convert the prosthesis from an anatomical to a reverse prosthesis, or vice versa, at a later time, by simply substituting the articular components attached to the anchors fixed to the bone without the need to remove the anchors.

The commonly used hybrid prostheses provide the usage of a glenoid anchor made of metallic material, called metal back, consisting of a flange having an at least partially convex proximal surface from which a hollow pin portion departs. The anchor is fixed to the glenoid cavity by inserting the pin in a hole which was previously formed substantially in the centre of the glenoid cavity till the proximal surface of the flange is in contact with the bone.

In case of anatomical prosthesis, a polyethylene insert is fixed on a distal surface of the flange.

Moving on the reverse prosthesis, the insert is removed and a convex glenoid articular component, called glenosphere, is fixed to the metal back by means of interposing an adapter which is axially inserted in the pin.

An alternative solution provides a glenoid anchor made up of only one hollow pin, without the flange, fixed to the glenoid cavity. In case of anatomical prosthesis, an insert is used which itself is made up of a flange from which a pin portion intended to be inserted within the pin glenoid anchor extends. Similarly to the previous solution, moving on the reverse prosthesis, the insert is removed and the glenosphere is mounted on an adapter which is in turn axially fixed within the pin.

The above-mentioned adapter provides a substantially elongated shape having a proximal end associated with the pin of the glenoid anchor and aligned to a distal end coupled to the glenosphere.

A glenoid anchor of the pin type together with a corresponding substantially circular flange insert with pin portion is also used in so-called (partial or total) resurfacing shoulder prostheses. Said prosthesis provides the usage of a glenoid insert which is at least partially inserted within the glenoid cavity such that the distal surface of the insert restores the continuity of the surrounding articular surface.

This in-depth implant mode is defined "inlay" or, alternatively, "inset". The insert is hold by the surrounding bone tissue in order to create a continuity between the existing articular surface and the component surface.

The pin anchor and the insert are usually small in size with respect to the previously described anatomical prostheses and are particularly recommended for treating glenoid defects in patients whose bone availability in the centre of the glene, which is useful for implanting a standard glenoid component, is low (for example A2 type glenoid morphology) or in patients in which the retroversion of the glene with deformity is such that the milling of the same, necessary for implanting a standard glenoid component, is not feasible due to the low bone availability (for example C or B3 type glenoid morphology) or when because of the glene erosion or conformation a standard implant (non "inset") would cause an excessive humeral lateralization and a corresponding over-tensioning of the surrounding soft tissues. In the above-mentioned patients, the humeral head should obviously not have an excessive subluxation level since it would be otherwise necessary to correct the glenoid version with "bone grafting" techniques or, where possible, "augmented" type glenoid prostheses where the availability of bone allows to prepare an adequate seat by means of milling.

Particularly, these small-sized implants can be locally placed at a determined area of the glenoid cavity in order to try to partially or totally restore the glenoid version without excessively milling the bone.

Nowadays, in case of inspection of a resurfacing prosthesis which needs the implant of a reverse prosthesis, both the insert and the pin anchor are removed and a further glenoid anchor of the reverse prosthesis is implanted by fixing it centrally to the glenoid cavity so as to have the centre of the glenosphere, which is coupled thereto, being aligned with the centre of the glenoid cavity.

For example, the international patent application No. WO 2019/079104 in the name of Imascap describes a reverse prosthesis implant which includes a prosthesis component having opposed offset pins to adjust the position of the center of the glenosphere of the reverse prosthesis. However, this implant is only for a reverse prosthesis and is not intended for a prosthesis conversion since it does not make use of an independent pivot anchor implanted in the glenoid cavity As a person skilled in the art well knows, the removal of a previously implanted pin anchor needs the removal of a part of the surrounding bone, thus making in some cases more difficult or even impossible the stable fixing of the reverse prosthesis.

Unfortunately, in these cases, even supposing to leave the pin anchor of the resurfacing prosthesis implanted and that glenosphere adapter can be inserted in such anchor, if such pin is displaced with respect to the centre of the glenoid cavity, by using a glenosphere adapter according to the prior art, the centre of the glenosphere would not be aligned with the centre of the glenoid cavity, thus determining a wrong cinematic of the whole reverse prosthesis.

The object of the present invention is to provide a glenoid adapter for shoulder prostheses having structural and functional characteristics such as to overcome the drawbacks reported with reference to the prior art and to allow the correct conversion from a resurfacing prosthesis to a reverse prosthesis without removing the glenoid anchor, regardless of where the resurfacing prosthesis is placed on the glene.

A further object of the present invention is furthermore to allow the correct placing of a convex articular component of reverse prosthesis in the absence of enough bone tissue not necessarily in the central area of the glenoid cavity.

SUMMARY OF THE INVENTION

The solution idea underlying the present invention is to provide an eccentric glenoid adapter wherein the fixing projection to the glenoid cavity is misaligned with respect to the attachment portion for the convex articular component of reverse prosthesis but usable with an already implanted glenoidal anchor. Advantageously, the fixing projection can be coupled with interference or Morse cone coupling with a pin glenoid anchor of a resurfacing prosthesis in order to provide the conversion to reverse prosthesis without removing the glenoid anchor, even if the latter is implanted in peripheral position, or at least not at the centre, of the glenoid cavity.

Based on such solution idea, a glenoid adapter for allowing a conversion from an anatomic resurfacing prosthesis to a reverse shoulder prosthesis, comprising:
- at least one fixing projection structured as an internally hollow pin having an own axis (X) and being arranged to be fixed to the glenoid cavity of the scapula through a glenoid anchor;
- a flange integral with said fixing projection;
- an attachment portion integral with the flange and extended in the direction opposite said fixing projection, as well as arranged to be coupled with an articular component of reverse prosthesis provided with a convex articular surface, said attachment portion having an own longitudinal axis (Y);
- characterized in that both the fixing projection and the attachment portion have truncated-cone shape and that the axis of the attachment portion (Y) is misaligned with respect to the fixing projection axis (X);
- said flange having a glenoid surface from which said fixing attachment rises.

Preferably, the fixing projection is arranged to be fixed to a glenoid anchor, which is in turn fixable to the glenoid cavity in a position displaced with respect to the centre of the glenoid cavity.

The glenoid anchor can advantageously be the same used in a resurfacing prosthesis in order to fix a polymeric insert at a defect of the articular surface of the glenoid cavity so as to recover the damaged articular surface.

In this way, the resurfacing prosthesis can be converted in reverse prosthesis by means of the adapter without having to remove the glenoid anchor, even if the latter is implanted in a non-central position of the glenoid cavity. The misalignment between the fixing projection and the attachment portion can be indeed advantageously chosen to position the centre of the convex articular component of the reverse prosthesis at the centre of the glenoid cavity of where it is considered more convenient in accordance with the glenohumeral morphology or with the relevant specific clinical-biomechanical needs.

The adapter can be indeed provided in different sizes of different dimensions and in different misalignments between fixing projection and attachment portion.

Alternatively, the adapter can be advantageously used for implanting a reverse prosthesis in case of lack of bone tissue in the central area of the glenoid cavity. In such case, a glenoid anchor can be implanted in a peripheral area of the glenoid cavity and the glenosphere can be applied by means of the adapter.

The fixing projection can be coupled to the glenoid anchor by means of cone-shaped coupling, and/or by means of a securing screw which crosses the projection and screws within the anchor.

Similarly, the attachment portion can be coupled to the convex articular component by means of cone-shaped coupling, and/or by means of a securing screw which crosses the convex articular component and screws within the attachment portion.

The adapter can be furthermore advantageously provided with a flange comprising a proximal surface arranged to be in contact with the glenoid cavity, and a distal surface opposite the proximal surface, with fixing projection which extends from the proximal surface in medial direction and the attachment portion which extends from the distal surface in side direction.

The flange can furthermore comprise a through-hole which crosses the flange from the proximal surface to the distal surface for passing at least one stabilization bone screw which can be inserted in the glenoid cavity.

The flange can furthermore have a substantially spherical-cap and/or provide at least one through-hole in a peripheral area close to the perimeter and/or at least one through-hole in a central area far from the perimeter.

BRIEF DESCRIPTION OF THE DRAWINGS

FIG. 10 shows a longitudinal section view of the adapter and the glenoid anchor taken according to the line A-A of FIG. 8;

FIG. 11 shows a longitudinal section view of the adapter and of the glenoid anchor taken according to the line B-B of FIG. 9;

FIG. 17 shows a longitudinal section view taken according to the line F-F of FIG. 15;

FIG. 18 shows a longitudinal section view taken according to the line G-G of FIG. 16;

FIG. 25 shows a longitudinal section view taken according to the line N-N of FIG. 23;

FIG. 26 shows a longitudinal section view of the assembly of FIG. 24 taken according to the line N-N of FIG. 23;

FIG. 27 shows a prospective view of the proximal part of a first assembled resurfacing prosthesis which can be converted to a reverse prosthesis by means of the adapter according to the present invention;

FIG. 28 shows a view of the proximal part of the resurfacing prosthesis of FIG. 27;

FIG. 29 shows a longitudinal section view taken according to the line B-B of FIG. 28;

FIG. 30 shows a prospective view of the proximal part of the resurfacing prosthesis of FIG. 27 which is disassembled;

FIG. 31 shows a longitudinal section view of the resurfacing prosthesis of FIG. 30;

FIG. 38 shows a longitudinal section view according to the line B-B of FIG. 36;

FIG. 39 shows a prospective view of the proximal part of a second assembled resurfacing prosthesis convertible to reverse prosthesis by means of the adapter according to the present invention;

FIG. 40 shows a prospective view of the proximal part of the resurfacing prosthesis of FIG. 39 which is disassembled;

FIG. 41 shows a view of the proximal part of the resurfacing prosthesis of FIG. 39;

FIG. 42 shows a longitudinal section view according to the line B-B of FIG. 41;

FIG. 43 shows a view of the proximal view of the resurfacing prosthesis of FIG. 40;

FIG. 44 shows a longitudinal section view according to the line B-B of FIG. 43.

DETAILED DESCRIPTION

Figure 2:
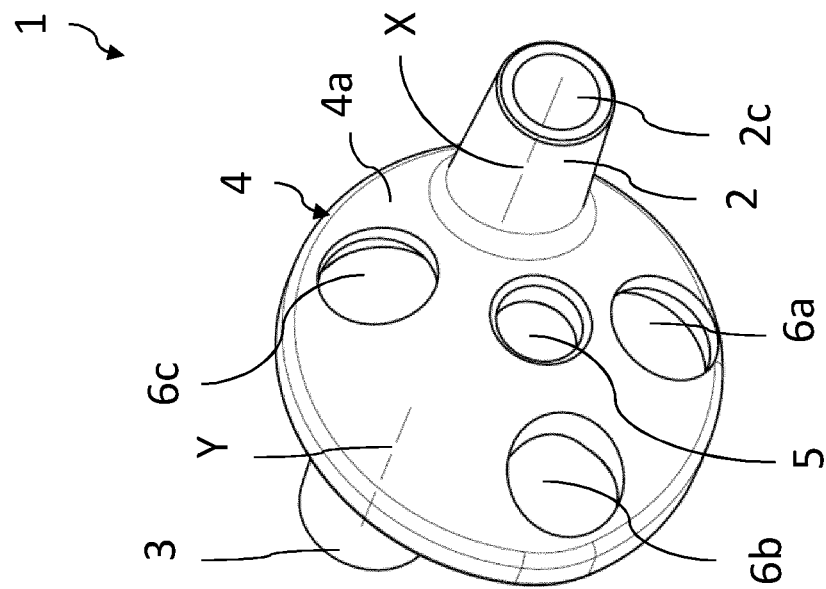
FIG. 2 shows a prospective view of the proximal part of the glenoid adapter of the FIG. 1.
Figure 1:
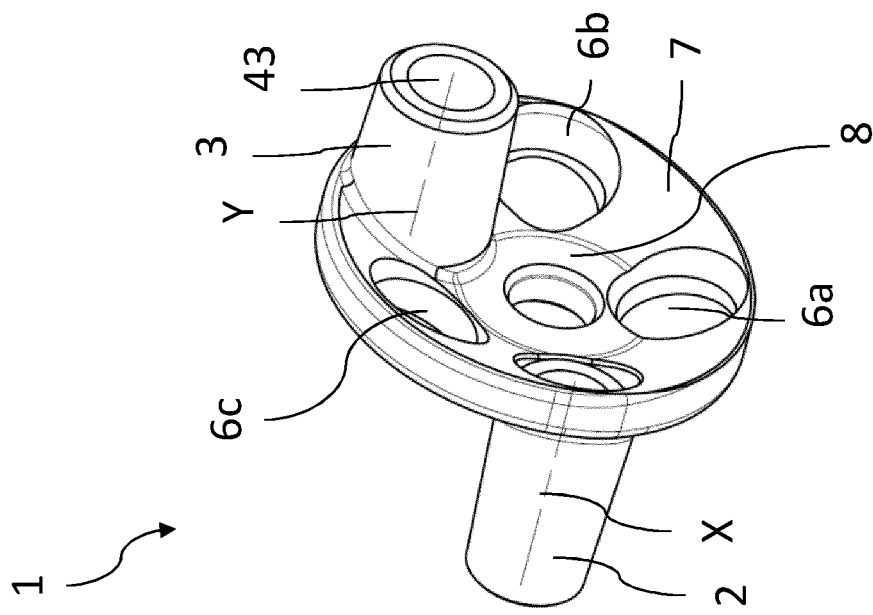
FIG. 1 shows a prospective view of the distal part of a glenoid adapter provided according the present invention.
Figure 5:
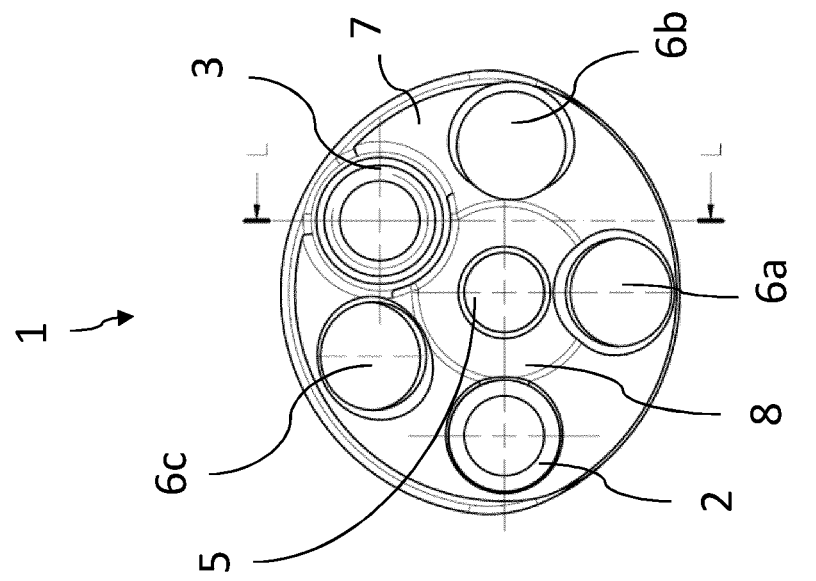
FIG. 5 shows a view of the distal part of the glenoid adapter of FIG. 1.
Figure 4:
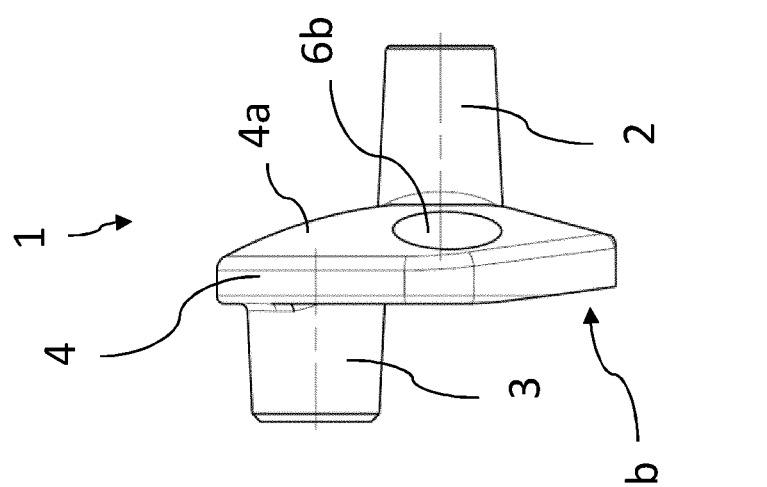
FIG. 4 shows a side view of the glenoid adapter of FIG. 1.
Figure 3:
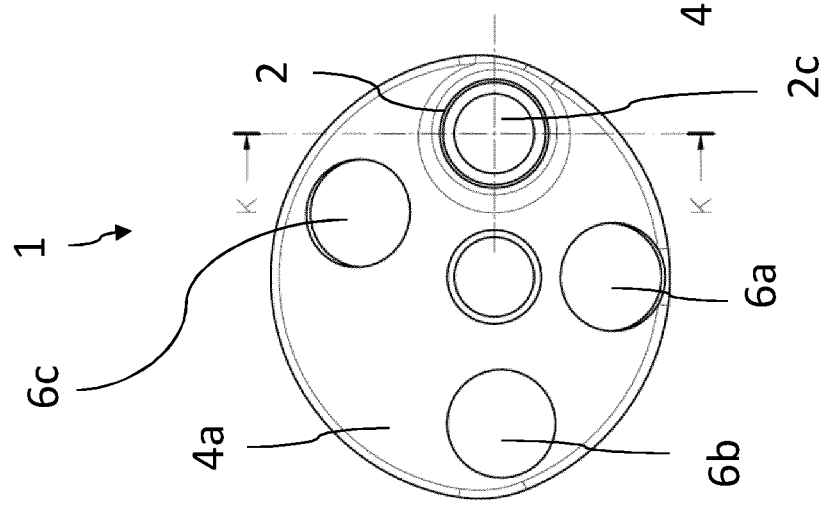
FIG. 3 shows a view of the proximal part of the glenoid adapter of FIG. 1.
Figure 7:
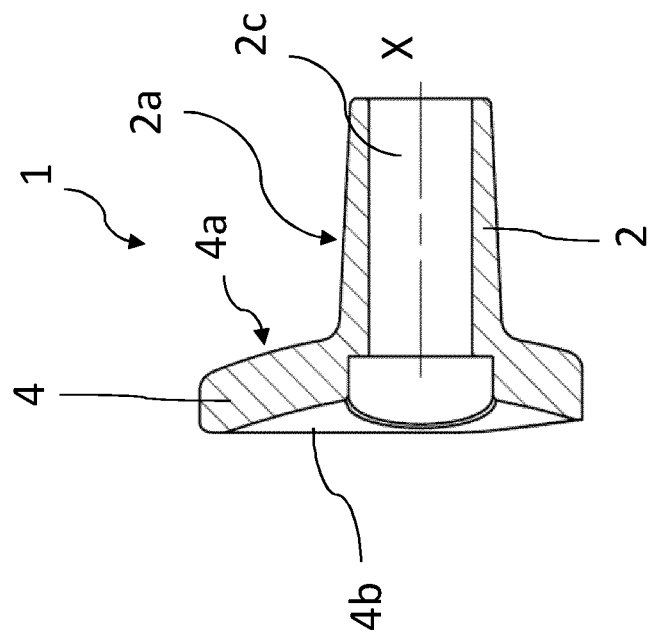
FIG. 7 shows a longitudinal section view taken according to the line K-K of FIG. 3.
Figure 6:
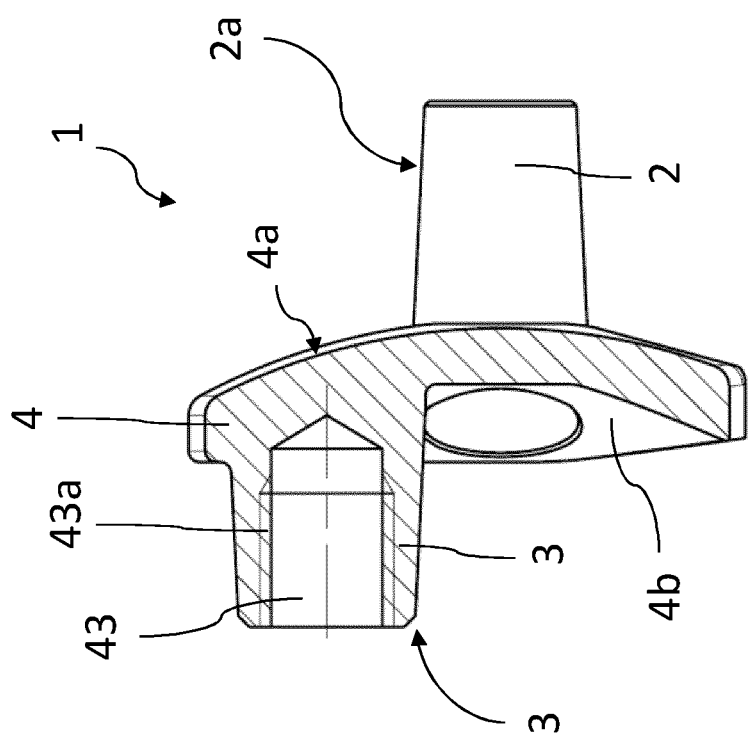
FIG. 6 shows a longitudinal section view taken according to the line L-L of FIG. 5.
Figure 8:
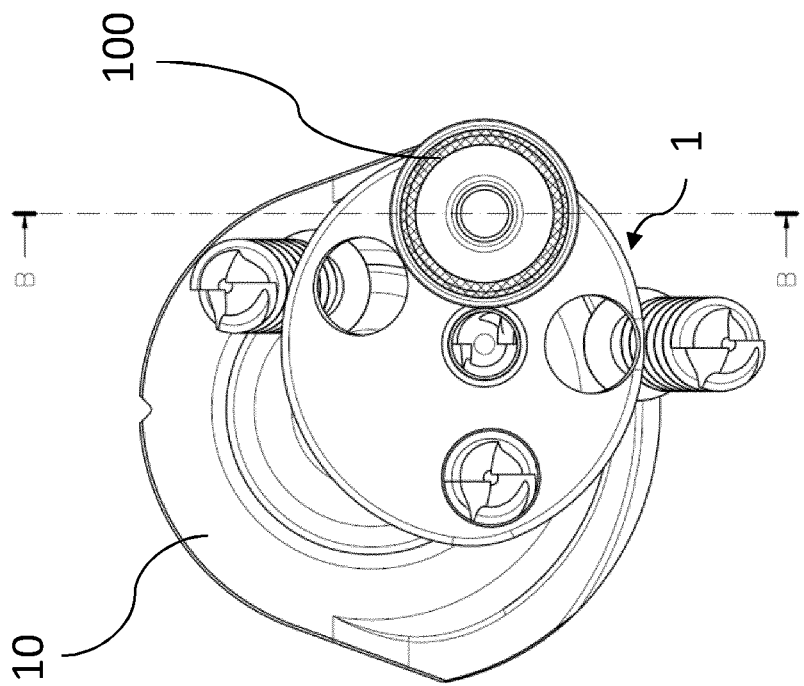
FIG. 8 shows a view of the proximal part of an assembly made up of the adapter of FIG. 1 cooperating with a convex articular component of reverse prosthesis, a pin glenoid anchor and stabilization bone screws.
Figure 9:
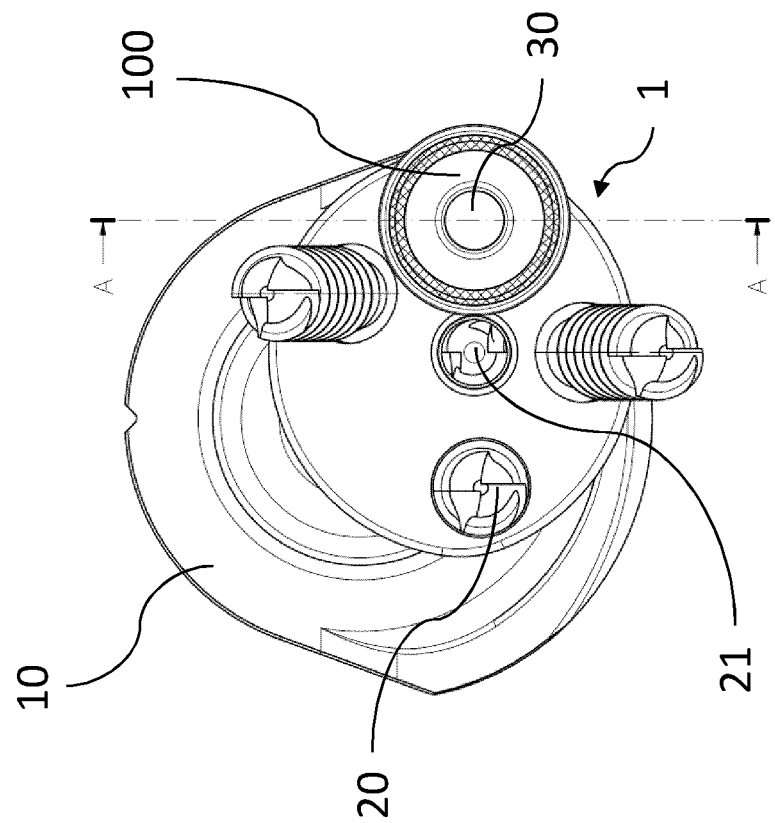
FIG. 9 shows a view of the proximal part of the assembly of FIG. 8 which is disassembled.
Figure 12:
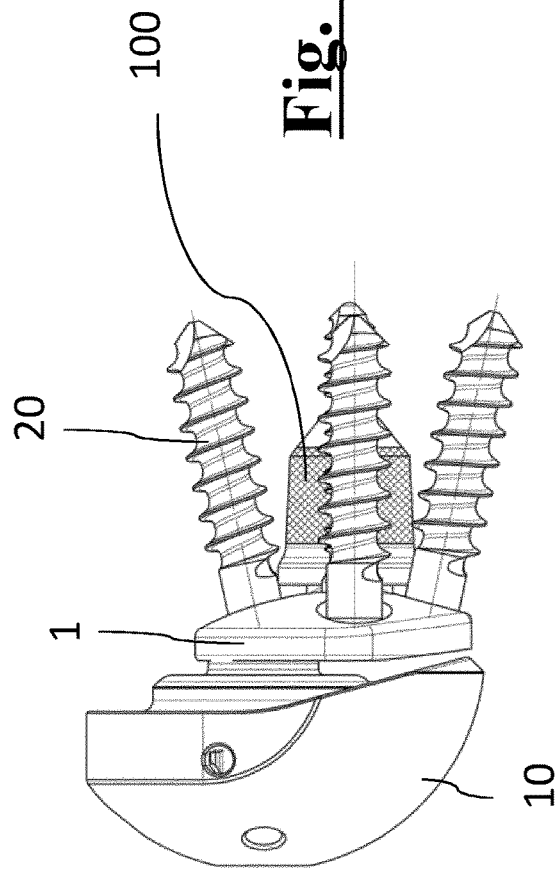
FIG. 12 shows a side view of the assembly of FIG. 8.
Figure 13:
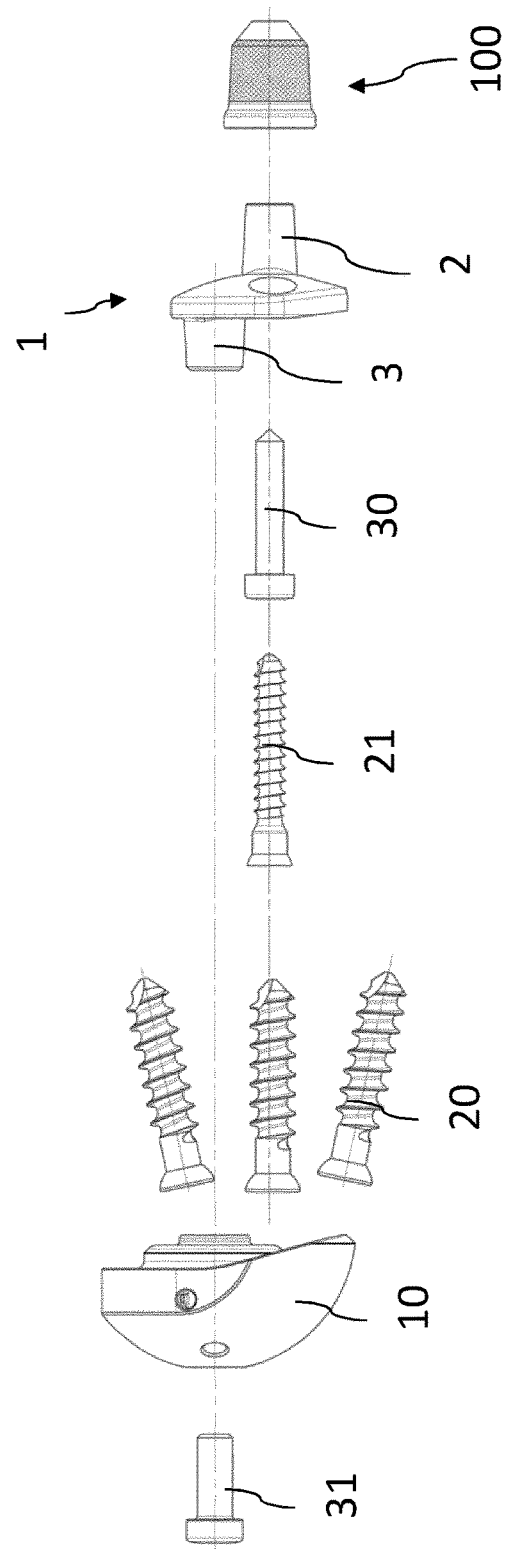
FIG. 13 shows a side view of the assembly of FIG. 9.
Figure 14:
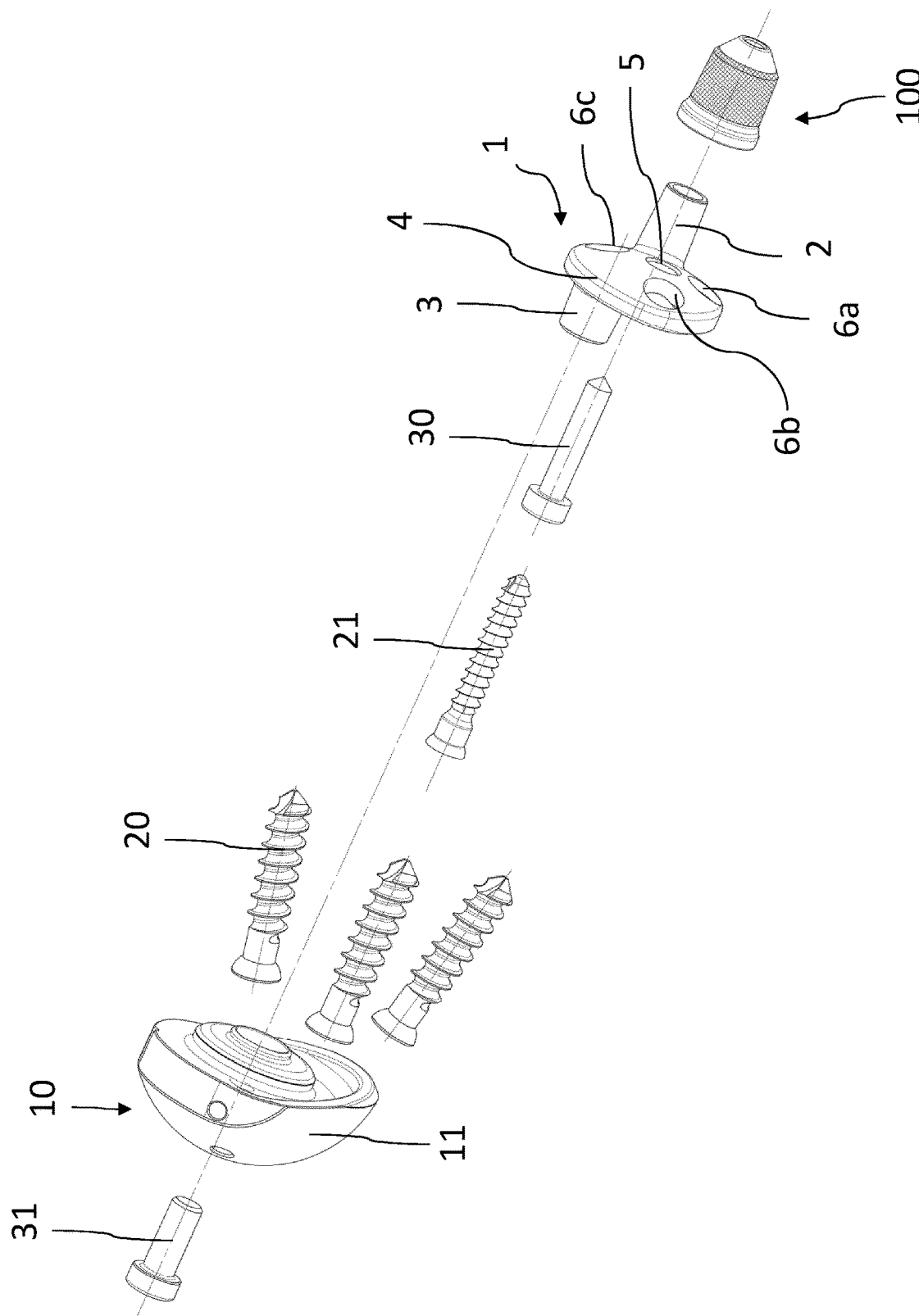
FIG. 14 shows a prospective view of the assembly of FIG. 9.
Figure 16:
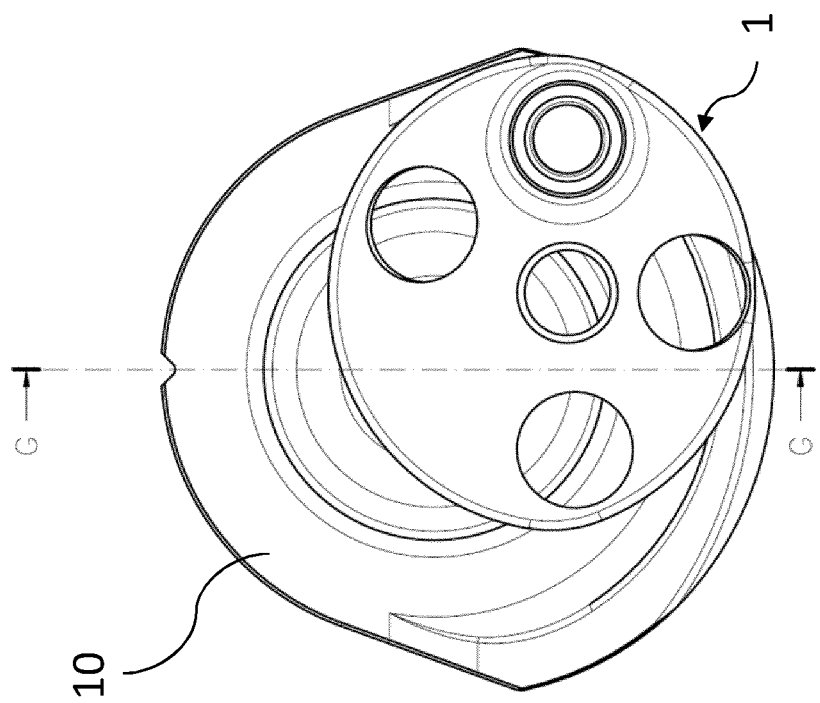
FIG. 16 shows a view of the proximal part of the assembly of FIG. 15 which is disassembled.
Figure 15:
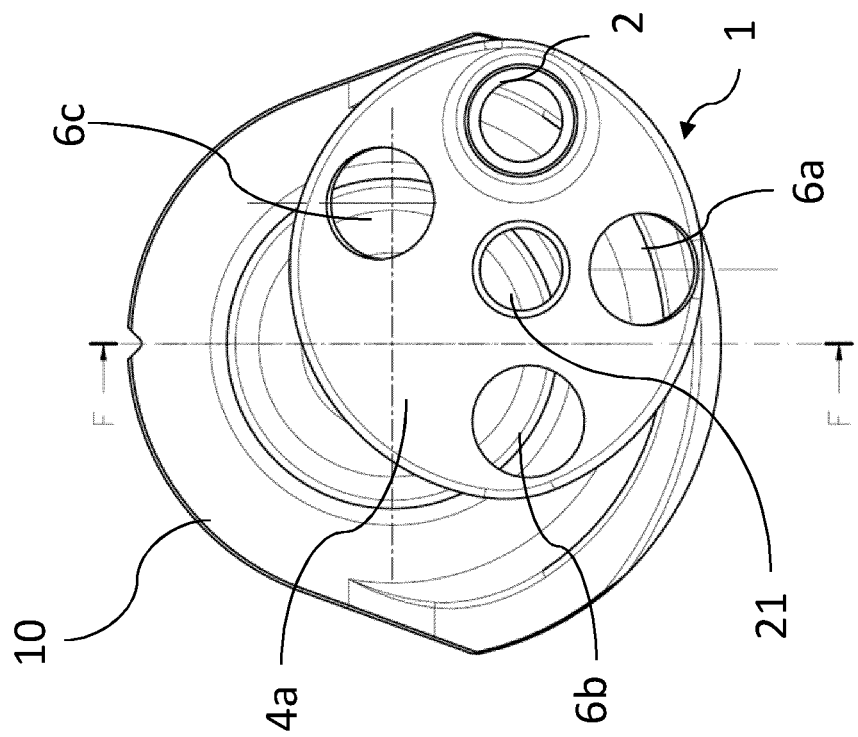
FIG. 15 shows a view of the proximal part of an assembly made up of the adapter of FIG. 1 cooperating with a convex articular component of reverse prosthesis.
Figure 20:
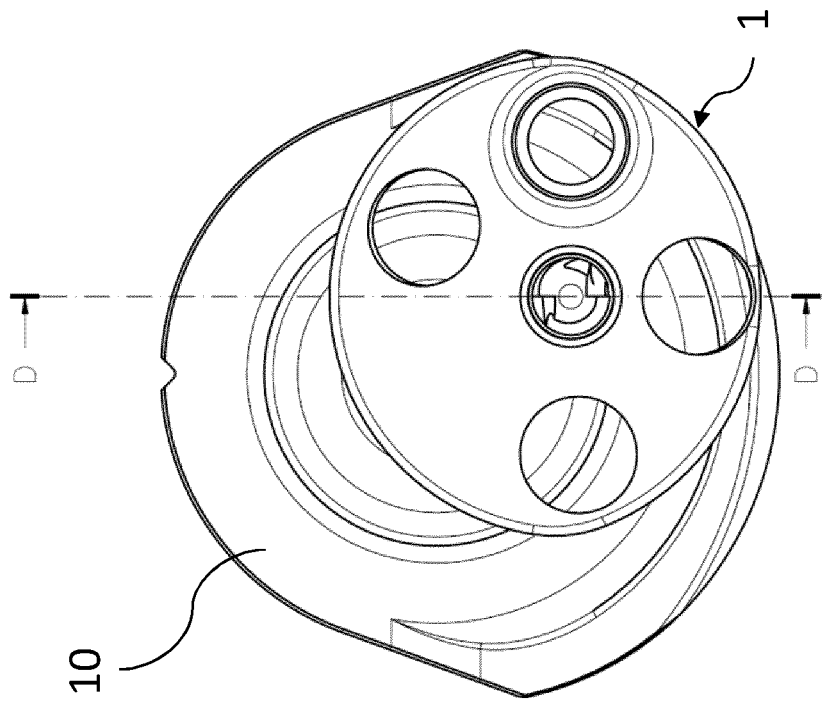
FIG. 20 shows a view of the proximal part of the assembly of FIG. 19 which is disassembled.
Figure 19:
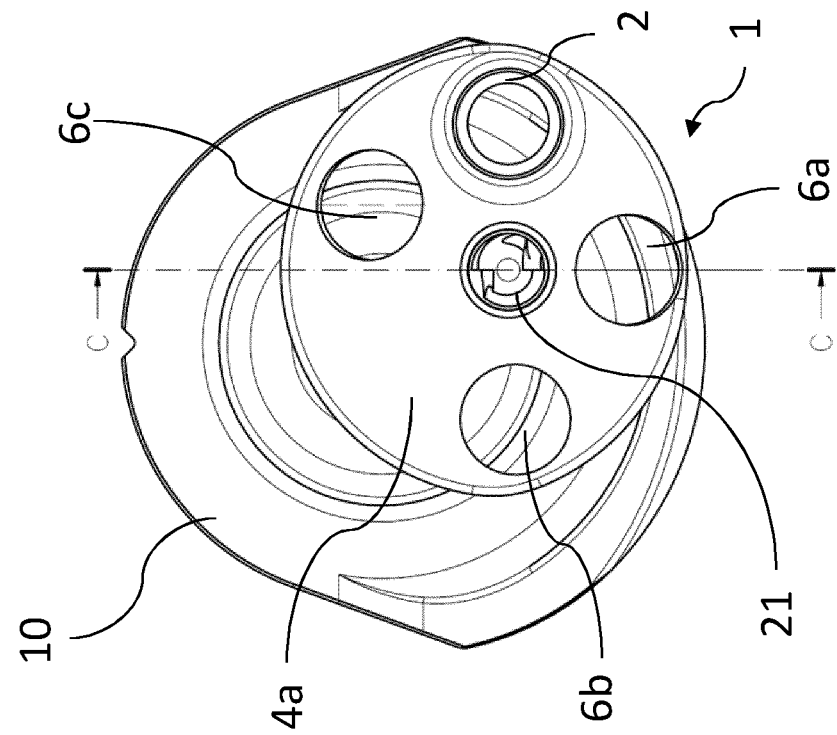
FIG. 19 shows a view of the proximal part of an assembly made up of the adapter of FIG. 1 cooperating with a convex articular component of reverse prosthesis and with a central stabilization bone screw.
Figure 21:
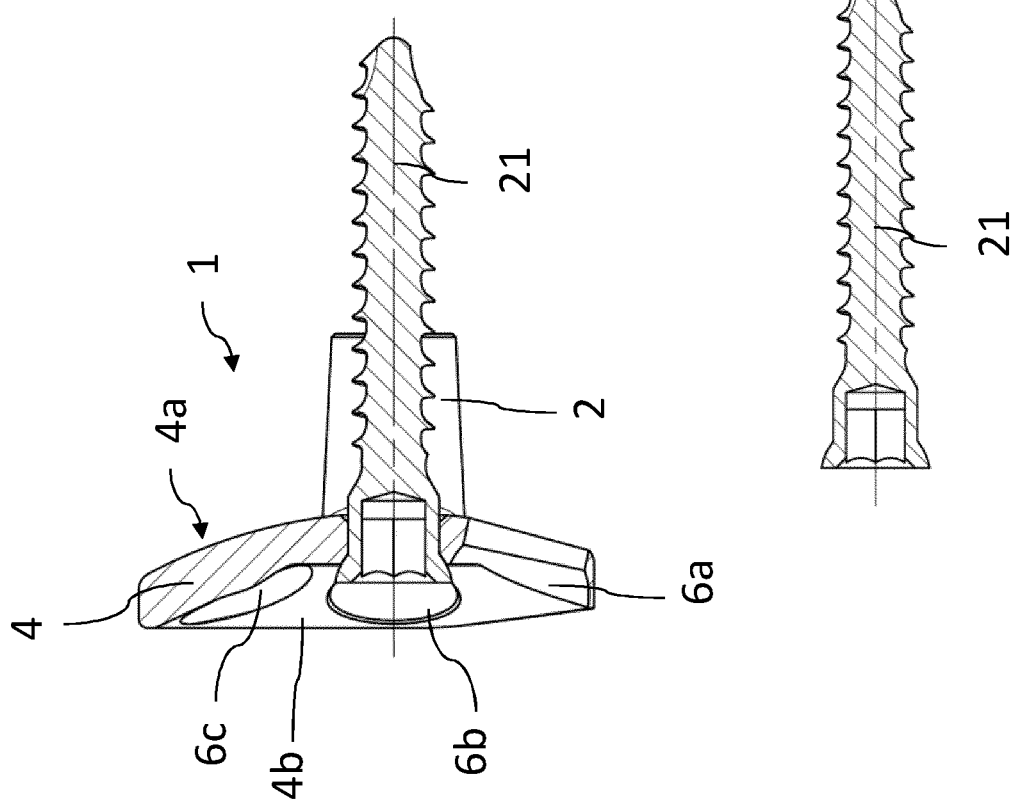
FIG. 21 shows a longitudinal section view of the adapter and of the central screw taken according to the line C-C of FIG. 19.
Figure 22:
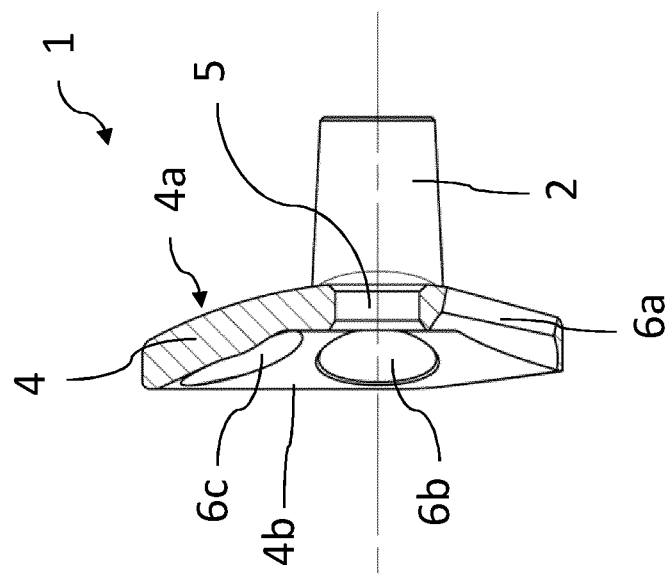
FIG. 22 shows a longitudinal section view of the adapter and of the central screw taken according to the line D-D of FIG. 20.
Figure 24:
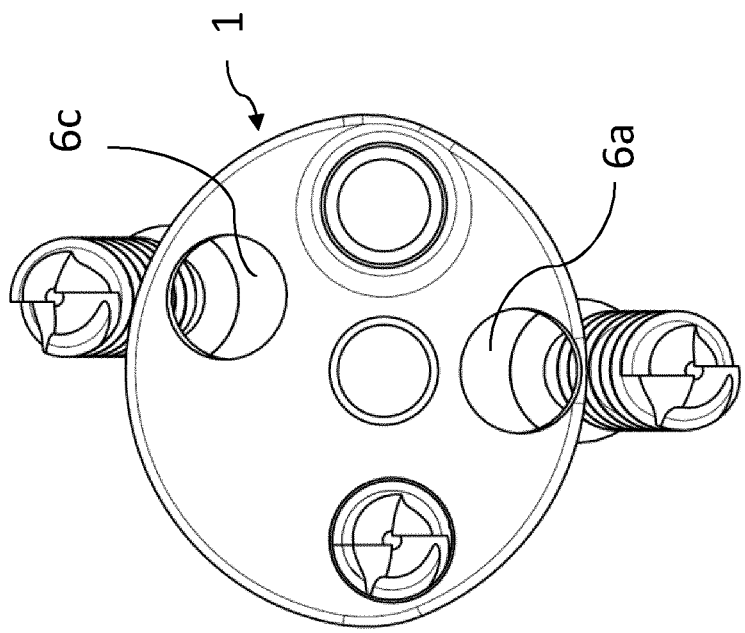
FIG. 24 shows a view of the proximal part of the assembly of FIG. 23 which is disassembled.
Figure 23:
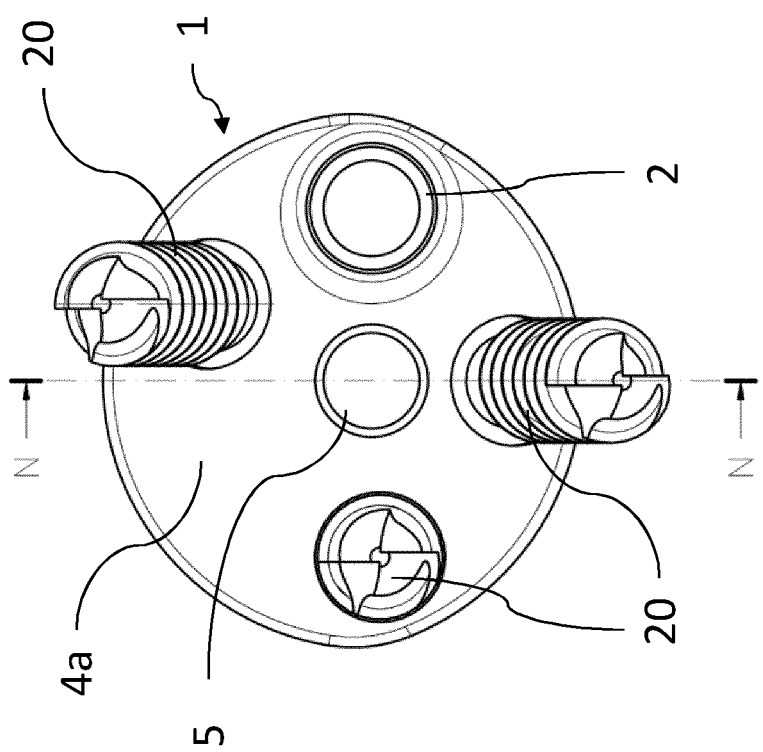
FIG. 23 shows a view of the proximal part of an assembly made up of the adapter of FIG. 1 cooperating with peripheral stabilization bone screws.

With reference to such figures, and in particular to FIGS. 1-7, a glenoid adapter 1, which is provided according to the present invention to allow a simple and correct conversion of a resurfacing shoulder prosthesis to reverse shoulder prosthesis, is globally and schematically designated with 1.

More generally, such adapter can be used for implanting a glenoid articular component of reverse prosthesis in cases where the glenoid anchor is already fixed or has to be fixed because of lack of bone tissue in a non-central area of the glenoid cavity. This does not obviously rule out the possibility to anyway use it with a central glenoid anchor to the glenoid cavity in case a displacement of the centre of the glenoid articular component with respect to centre of the glenoid cavity is needed.

In the remainder of the description, this glenoid adapter 1 will be referred to with the simpler term of adapter 1.

In the below described example of application, the adapter 1 is intended to be fixed to a glenoid anchor 100 in turn fixable in a glenoid cavity 301 of a scapula 300, in particular in a displaced position with respect to the centre of said glenoid cavity 301.

As it will be evident from the example shown in the following, the adapter 1 is particularly useful in case of converting a resurfacing prosthesis 400, 400' to reverse prosthesis, when a glenoid anchor 100 of the resurfacing prosthesis is fixed in a decentralized position in the glenoid cavity. This does not obviously rule out the possibility that the glenoid anchor 100 could be the anchor of a traditional anatomical shoulder prosthesis or an anchor used for implanting a reverse prosthesis by means of the adapter 1.

FIGS. 27-31 shows two main components of a resurfacing prosthesis 400: a pin anchor 100 within which the fixing projection 2 of the adapter 1 is fixable and an insert 200 which is also fixable within such glenoid anchor 100.

The glenoid anchor 100 is of the type with internally hollow pin and extends from an open proximal end 111 to a tapered medial end 120. The proximal end 111 ends up in an internal cavity 110 which merges in a medial hole 121 passing at the medial end 120. The proximal opening, the internal cavity and the medial hole concentrically come in succession along a common longitudinal symmetry axis J of the glenoid anchor 100. The medial hole 121 is internally threaded for engaging a first securing screw 30 during screwing, as will be evident in the following.

The internal cavity 110 is delimited by an interference or Morse cone-shaped coupling having an internal conical surface 112, that is slanting with respect to the anchor axis J causing the reduction of the internal diameter of the cavity in direction of the medial end 120.

The insert 200 of the resurfacing prosthesis has an insert flange 201 from which an insert pin 202, which can be coupled with interference or Morse cone coupling with the internal cavity 110 of the glenoid anchor 100, extends. The insert 200 is furthermore provided with an insert medial edge 203 received in a snapping manner within an annular medial recess 115 of the glenoid anchor 1 which is connecting with internal cavity 110 in a side direction and with hole 121 in a medial direction. Tooth 204 are placed close to the flange 201 and are arranged to prevent the rotation of the insert 200 by means of the opposed notches 116 at the proximal end 111 of the glenoid anchor 1.

The insert 200 has a substantially circular shape, called "button-like". Such insert 200 is usually small in size, such that it can be placed in a determined area of the glenoid cavity in which there is a defect.

In case of glenoid defects which extend to the most part of the glenoid cavity, as alternative to a common "onlay" anatomical prosthesis, a second resurfacing prosthesis 400' can be used which, unlike the above-described resurfacing prosthesis 400, adopts a second larger insert 200' and which is above all of different shape.

The insert 200' is also of the "inlay" type, that is arranged to be deeply implanted in the glenoid cavity and to be hold by the surrounding bone.

For this purpose, the insert 200', shown in the FIGS. 39-44, has a substantially pear-like shape.

In other words, the insert 200' comprises a first substantially semicircular portion 201a' and a second substantially semicircular portion 201b' which are jointed together, wherein the first portion has a radius of curvature which is lower than the one of the second portion.

Compared to a common insert for "onlay" anatomical prosthesis, for housing the insert 200', the glenoid cavity is made by removing more bone tissue in depth but saving bone around the insert. This bone saving can be particularly advantageous in case of prosthesis inspection with a larger implant. The insert 200' can provide at least one peripheral stabilization element 205', preferably one at the first portion 201a' and one at the second portion 201b' which extends in the same direction of the insert pin 202. The stabilization elements 205' are substantially pins arranged to be cemented in the bone so as to further fix the insert 200' to the bone.

In case of conversion of the resurfacing prosthesis 400, 400' to reverse prosthesis, the adapter 1 can be advantageously used for implanting a glenoid articular component 10 of reverse prosthesis without having to remove the glenoid anchor 100. In particular, it will be enough to extract the insert 200 from the glenoid anchor 100 and to couple the fixing projection 2 of the adapter 1 within the glenoid anchor 100 as will be apparent in the following.

The conversion by using the adapter 1 is particularly advantageous in the case where the glenoid anchor 100 is inserted in a peripheral position of the glenoid cavity 301, since, thanks to the misalignment between fixing projection and attachment portion, the glenoid articular component 10 can be centred with the centre of the glenoid cavity 301. But even if the glenoid anchor 100 is implanted in a central position, the adapter 1 can be used for decentralizing the articular component of the reverse prosthesis, for example more downwards.

Going back to the adapter 1, it is structurally independent and comprises at least one fixing projection 2 integral with and opposite to an attachment portion 3. The fixing projection 2 and the attachment portion 3 are integral with a flange 4 and are extended in directions opposite with respect to the flange 4.

The fixing projection 2 has an own longitudinal axis which will be called axis X in the following and is arranged to be inserted within the internal cavity 110 of the glenoid anchor 100.

The portion attachment 3 has an own longitudinal axis which will be called axis Y and is arranged for coupling with a convex glenoid articular component 10 of reverse prosthesis, known as glenosphere.

The axis X of the fixing projection 2 and the axis Y of the attachment portion 3 are advantageously misaligned with respect to one another. In one embodiment, such axes X and Y are also parallel to each other.

In this way, the adapter 1 allows the point to be misaligned in which the constraint with the glenoid cavity is provided and the point in which the glenosphere is attached. If the point, in which the constraint with the bone is provided, is placed in a peripheral area of the glenoid cavity, the adapter can be dimensioned such that the misalignment between the fixing projection and the attachment portion is such to have the centre of the glenosphere at a selected point, such as for example the centre of the glenoid cavity, thus guaranteeing a correct cinematic of the shoulder prosthesis. In some cases, it can be useful to displace the centre of the glenosphere with respect to the glenoid cavity, for example slightly lower, in order to reduce the so-called "scapular notch".

The flange 4 has a substantially spherical-cap shape with a circular perimetral edge and with a convexity on the side of the fixing projection 2 and a concavity on the side of the attachment portion 3. The fixing projection 2 is formed integrally with the flange 4 and projecting therefrom in a decentralized area and close to the perimetral edge of the flange 4. Similarly, the attachment portion 3 is in turn formed integrally with the flange 4 but on the opposite side of the flange 4 and in a decentralized area which is still close to the perimetral edge of the flange 4, as will be described in more detail below.

The flange 4 can be particularly small in size and slightly wider than the respective bases of the fixing projection 2 and of the attachment portion 3 but anyway such as to guarantee the misalignment between the axes X and Y.

The fixing projection 2 comprises an external surface 2a which can be inserted within the internal cavity 110 of the glenoid anchor 100 by means of cone-shaped coupling with the internal surface 112. This does not rule out the possibility that it can be used in a different coupling type known in the field.

The external surface 2a particularly defines a truncated cone with external diameter which decreases in a medial direction.

The fixing projection 2 is axially crossed by a projection through-hole 2c in which a first securing screw 30 having a thread, which can be engaged during screwing with the medial hole 121, can be inserted when the fixing projection 2 is inserted in the internal cavity 110 of the glenoid anchor 100. In this way, the adapter 1 secured to the glenoid anchor 100 maintaining the contact between the respectively internal 112 and external 2a cone-shaped surfaces of the glenoid anchor 100 and of the fixing projection 2.

This does not rule out the possibility that, in alternative embodiments, the fixing projection is fixed only by means of cone-shaped coupling or only by means of a securing screw within the glenoid anchor 100 or directly in the bone.

The attachment portion 3 has also a truncated-cone shape defined by an external attachment surface 3a with external diameter which is decreasing in a distal direction.

The attachment portion 3 comprises a dead-end cylindrical cavity 43 which opens itself to a distal end of the attachment portion 3a. Such cylindrical cavity 43 has an internal thread 43a arranged to receive, during screwing, a second securing screw 31 for fixing a glenoid articular component 10 of reverse prosthesis to the adapter 1.

An example of a glenoid articular component 10 of reverse prosthesis associable with the attachment portion 3 is made up of a so-called glenosphere having a distal convex articular surface 11 and a proximal coupling portion 12 (see for example FIGS. 15-18).

The coupling portion 12 comprises a coupling cavity 13 having an internal coupling surface 13a with internal profile such as to allow insertion by means of cone-shaped coupling of the attachment portion 3 of the adapter 1.

This does not rule out the possibility to use other types of coupling.

The coupling cavity 13 distally merges in an opening 14 obtained at the distal convex articular surface 11 of the convex articular component 10.

The second securing screw 31 can then be inserted in the opening 14, through the coupling cavity 13 until it engages during screwing within the cylindrical cavity 43 of the adapter 1 when inserted within the coupling cavity 13 of the glenoid articular component 10.

This does not rule out the possibility that, in alternative embodiments, the attachment portion is fixed only by means of cone-shaped engagement or only by means of a securing screw to a glenoid articular component of reverse prosthesis.

As previously said, the adapter 1 furthermore comprises the flange 4 having a convex proximal surface 4a arranged to be in contact with the previously made glenoid cavity 301 and a concave distal surface 4b opposite the proximal surface 4a. Alternative embodiments can obviously provide different conformations of the distal and/or proximal surfaces, for example they can be plane surfaces.

The fixing projection 2 medially extends from the proximal surface 4a, while 1a attachment portion 3 laterally extends, that is in an opposite direction, from the distal surface 4b.

The flange 4 is crossed by at least one through-hole 5, 6a, 6b, 6c which extends from the proximal surface to the distal one for inserting corresponding stabilization bone screws 20, 21 into the glenoid cavity 301.

The adapter 1 has a substantially spherical-cap shape with substantially circular perimetral profile.

In one of the possible embodiments of the present disclosure the distal surface 4b of the flange 4 is divided into two areas: a peripheral area 7 which surrounds a circular central area 8.

Both the attachment portion axis Y and the fixing projection axis X intersect the peripheral area 7 such that the cylindrical cavity 43 of the attachment portion 3 and the projection through-hole 2c of the fixing projection 2 are placed at such peripheral area 7. As an alternative, one of the two axis X or Y can be central.

At the peripheral area 7, peripheral through-holes 6a, 6b, 6c are obtained for inserting corresponding peripheral stabilizing bone screws 20 for further fixing of the flange 4 to the glenoid cavity 301.

At the central circular area 8, a central through-hole 5 is obtained having a central hole axis parallel to the axes X and Y for inserting a central stabilizing bone screw 21 for further fixing of the flange 4 to the glenoid cavity 301.

With reference to the FIGS. 32-38, a method for converting a resurfacing prosthesis 400 to a reverse prosthesis by using the adapter 1 will now be described.

A similar method can be used to also convert an anatomical prosthesis which uses a glenoid anchor similar to the one used by a resurfacing prosthesis.

Figure 33:
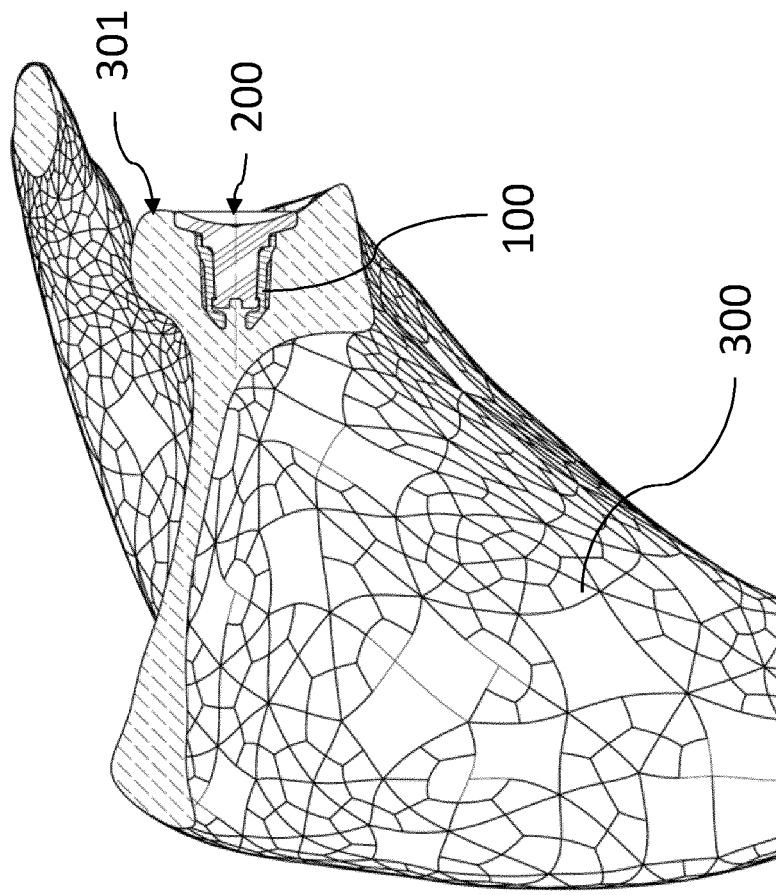
FIG. 33 shows a longitudinal section view taken according to the line A-A of FIG. 32.
Figure 32:
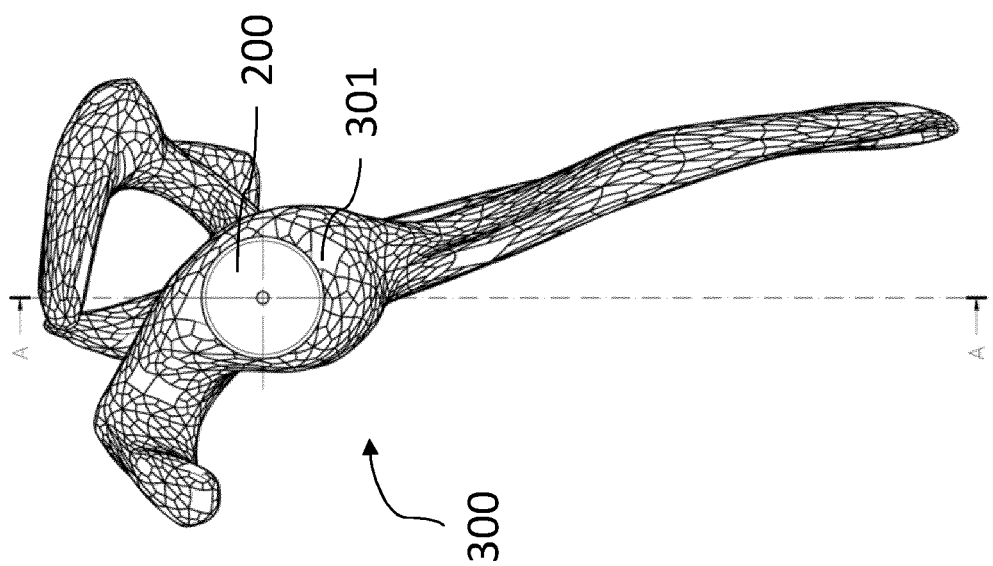
FIG. 32 shows a sagittal view of a scapula model with a resurfacing prosthesis of FIG. 28 which is implanted.

FIGS. 32-33 shows a resurfacing prosthesis 400 implanted in the glenoid cavity 301 of a scapula model 300 with the insert 200 inserted in a snapping manner in the glenoid anchor 100 which is in turn fixed in a hole formed in the bone.

Figure 35:
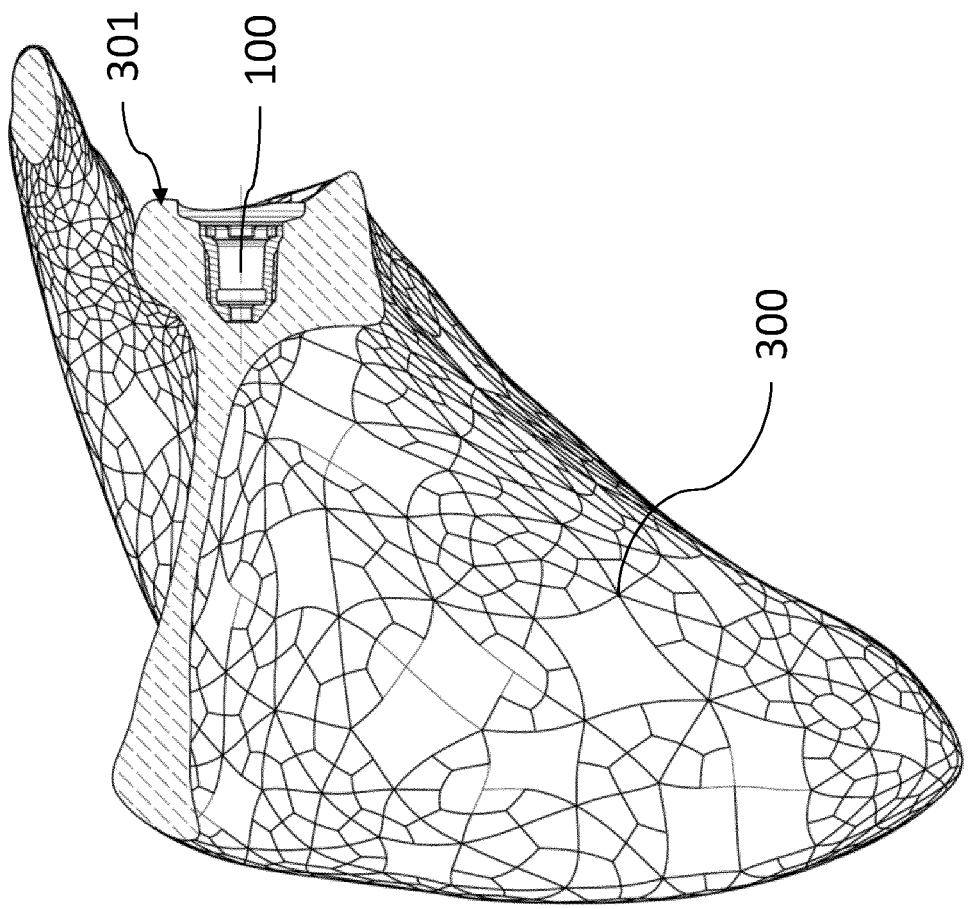
FIG. 35 shows a longitudinal section view taken according to the line A-A of FIG. 34.
Figure 34:
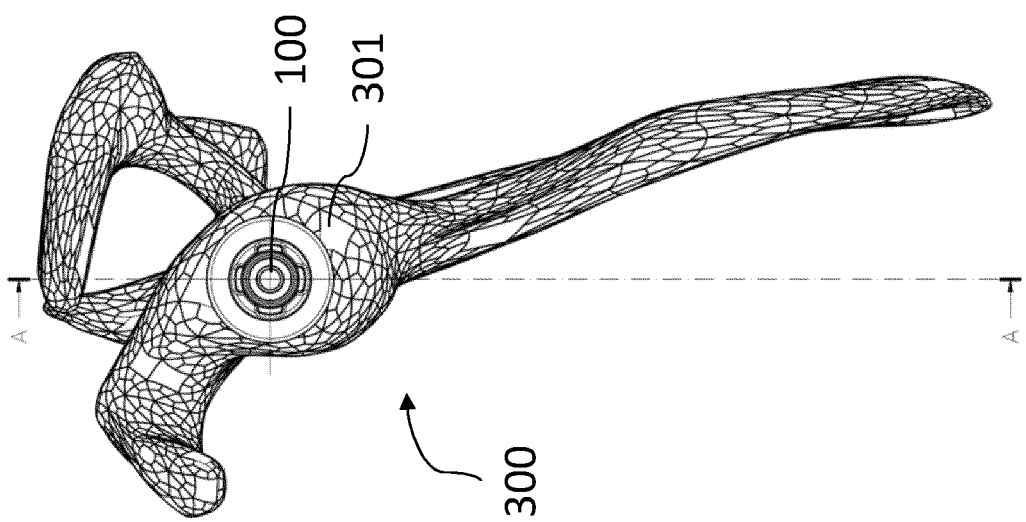
FIG. 34 shows a sagittal view of a scapula model with only the glenoid anchor of the resurfacing prosthesis of FIG. 28 which is implanted.
Figure 37:
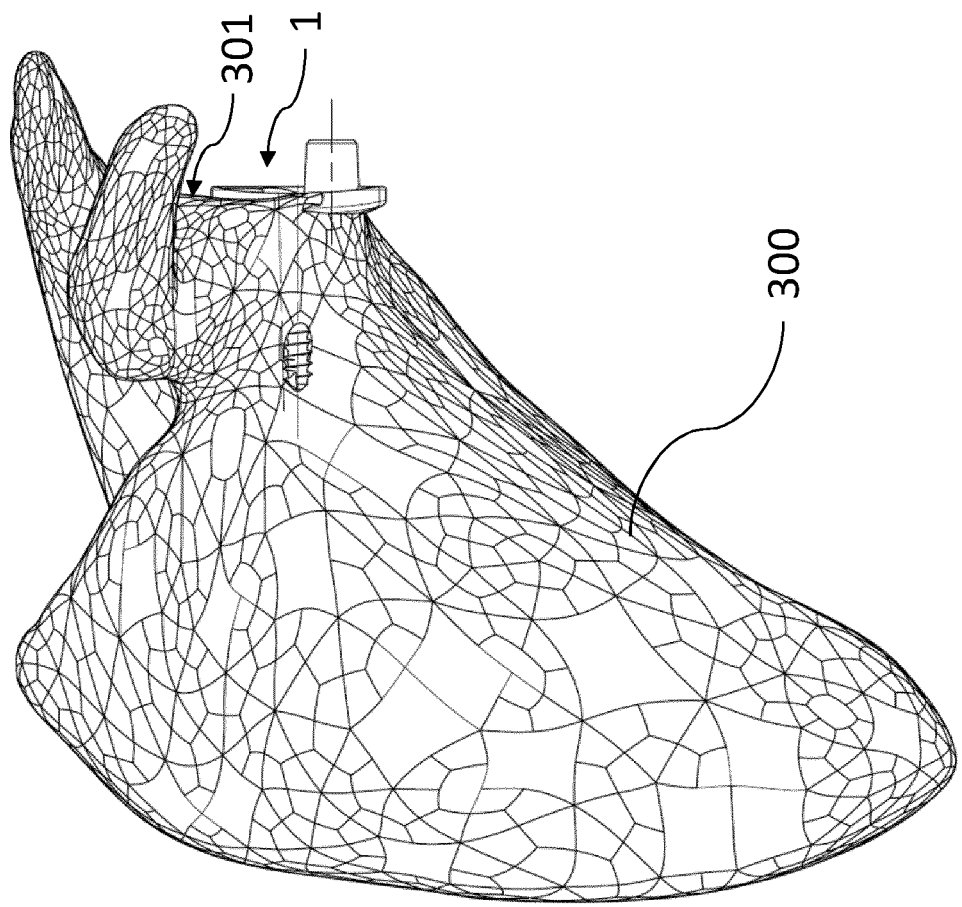
FIG. 37 shows a coronal view of a scapula model with the glenoid anchor of FIG. 34, which is implanted, to which a glenoid adapter of FIG. 1 is associated.
Figure 36:
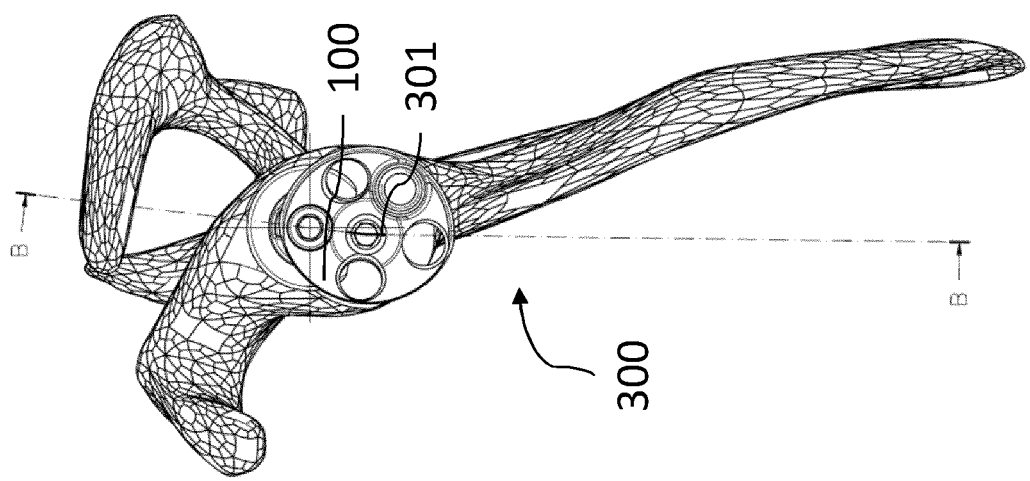
FIG. 36 shows a sagittal view of a scapula model with the glenoid anchor of FIG. 34, which is implanted, to which a glenoid adapter of FIG. 1 is associated.

For passing to a reverse prosthesis, it is enough to remove the insert 200 from the glenoid anchor 100 leaving the glenoid anchor 100 implanted in the glenoid cavity 301, as shown in the FIGS. 34-35.

The glenoid adapter 1 is then fixed to the glenoid anchor 100 by inserting the fixing projection 2 of the adapter 1 within the internal cavity 110 of the glenoid anchor 100 and causing the proximal surface 4a of the flange 4 to adhere to the glenoid cavity 301.

The fixing projection 2 can be then further secured to the anchor 100 by inserting the first securing screw 30 at the open end 110 of the anchor 100 until the medial hole 121 of the medial end 120 is engaged during screwing.

The flange 4 of the adapter 1 can be furthermore fixed at the glenoid cavity 301 by inserting peripheral stabilization screws 20 in the respective peripheral through-holes 6a, 6b, 6c and the central stabilization screw 21 in the central through-hole 5.

Finally, the glenoid articular component 10 of reverse prosthesis is fixed to the attachment portion 3 of the adapter 1, by inserting the attachment portion 3 within the coupling internal cavity 13 of the glenoid articular component 10.

The glenoid articular component 10 can be then further secured to the anchor 100 by inserting the second securing screw 31 at the opening 14 of the articular component 10, through the coupling cavity 13 of the attachment portion 2 of the adapter 1, until it engages during screwing within the cylindrical cavity 43.

From the previous description clearly emerges that the glenoid adapter according the present invention achieves the intended purposes and accomplishes various advantages, of which the main will be listed below.

Basically, with the solution of the present invention, it is provided that the fixing projection of the glenoid adapter is not aligned with the attachment portion for the convex articular component of reverse prosthesis. In this way, by conveniently dimensioning the misalignment between fixing projection and attachment portion, it is possible to position the centre of the non-aligned articular component with the fixing point of the adapter to the glenoid anchor.

This solution is particularly useful for converting a resurfacing prosthesis in a reverse prosthesis in a simple, fast and slightly invasive manner, in particular in the case where the glenoid anchor of the resurfacing prosthesis is implanted in a peripheral area of the glenoid cavity, or at least not in a central position.

Using the adapter according the present invention, the reverse prosthesis can be implanted without having to remove the glenoid anchor of the resurfacing prosthesis, thus guaranteeing the alignment of the centre of the articular component of reverse prosthesis with the centre of the glenoid cavity or in another position according to the clinical needs by conveniently rotating the adapter 1 and consequently guaranteeing a correct cinematic of the reverse shoulder prosthesis.

In this way, the conversion of the prosthesis from anatomical to inverse will allow the axis of the glenosphere to be repositioned in the most convenient position in a less invasive and more conservative way as regards the bone, leaving the well osseo-integrated pin anchor in place.

For the conversion, it is enough to remove the insert from the glenoid anchor and to couple the fixing projection of the adapter within the anchor. The articular component of reverse prosthesis will be then fixed to the attachment portion.

The adapter can be provided in more than one size so as to allow the surgeon to choose the optimal misalignment between fixing projection and attachment portion during the implant in order to have the correct positioning of the articular component.

The adapter can be also used to implant a reverse prosthesis by means of a glenoid anchor also in situations where the central area of the glenoid cavity has a lack of bone tissue. In such case, the glenoid anchor can be implanted in a peripheral area of the glenoid cavity where there is more bone and, by means of the glenoid adapter according to the present invention, it can correctly position the convex articular component of reverse prosthesis.

What is claimed is:

1. A glenoid adapter for allowing a conversion from an anatomic resurfacing prosthesis to a reverse shoulder prosthesis, comprising:
    at least one fixing projection structured as an internally hollow pin having an own axis and being arranged to be fixed to the glenoid cavity of the scapula through a glenoid anchor;
    a flange integral with said fixing projection;
    an attachment portion integral with the flange and extended in a direction opposite said fixing projection, as well as arranged to be coupled with an articular component of reverse prosthesis provided with a convex articular surface, said attachment portion having an own longitudinal axis;
    wherein both the fixing projection and the attachment portion have truncated-cone shape and wherein the axis of the attachment portion is misaligned with respect to the fixing projection axis;
    said flange having a glenoid surface from which said fixing projection rises.

2. The adapter according to the claim 1, wherein said truncated-cone shaped fixing projection is arranged to be fixed to said glenoid anchor, which is in turn fixable to said glenoid cavity through a security screw.

3. The adapter according to claim 2, wherein said glenoid anchor is an internally hollow pin and has a medial end and an open proximal end communicating with an internal cavity being in turn defined by an internal surface; said fixing projection of said adapter comprising an external surface which can be coupled with interference or Morse cone coupling with said internal surface of said internal cavity.

4. The adapter according to claim 3, wherein said external surface is cone-shaped and said internal surface of the glenoid anchor cavity is also cone-shaped.

5. The adapter according to claim 3, wherein said medial end of said glenoid anchor is opened by a hole, which communicates with said internal cavity; said fixing projection comprising a projection through-hole for inserting a first securing screw which can be engaged during screwing within said hole of said glenoid anchor.

6. The adapter according to claim 1, wherein said flange comprises a preferably convex proximal surface arranged to be in contact with said glenoid cavity, and a distal surface opposite to said proximal surface; said fixing projection extending in medial direction from said proximal surface; said attachment portion extending in a side direction from said distal surface.

7. The adapter according to claim 6, wherein said flange has a substantially spherical-cap shape, said fixing projection axis intersecting a peripheral area of said proximal surface.

8. The adapter according to claim 6, wherein said flange has a substantially spherical-cap shape, said attachment portion axis intersecting a peripheral area of said proximal surface.

9. The adapter according to claim 6, wherein said flange comprises at least one through-hole which crosses said flange from said proximal surface to said distal surface for passing at least one stabilization bone screw, which can be inserted in said glenoid cavity.

10. The adapter according to claim 9, wherein at least one central through-hole is substantially formed in the centre of said proximal surface.

11. The adapter according to claim 9, wherein said flange has a substantially spherical-cap shape, at least one peripheral through-hole being formed at a peripheral area of said proximal surface.

12. The adapter according to claim 1, wherein said attachment portion comprises a threaded cylindrical cavity; said articular component of reverse prosthesis being associable with said attachment portion by means of a second securing screw engaging with said cylindrical cavity.

13. The adapter according to claim 1, wherein said attachment portion comprises an external attachment surface couplable in contact with an internal coupling surface of said articular component.

14. The adapter according to the claim 13, wherein said external attachment surface is cone-shaped and said internal coupling surface is also cone-shaped.

15. A reverse shoulder joint prosthesis comprising:
    a glenoid adaptor according to claim 1;
    a glenoid anchor of a resurfacing prosthesis, within which the fixing projection of the glenoid adapter is fixed; and
    a convex articular component of inverse prosthesis coupled with the attachment portion of the glenoid adapter.

16. A method for converting a resurfacing prosthesis to a reverse prosthesis by using an adapter according to claim 1, comprising the steps of:
    removing an insert from a glenoid anchor of a resurfacing prosthesis implanted in a glenoid cavity of a scapula, leaving the glenoid anchor implanted in the glenoid cavity;
    fixing a glenoid adapter according to claim 1 to said glenoid anchor by inserting the fixing projection of the adapter within an internal cavity of the glenoid anchor and causing a proximal surface of the flange to adhere to the glenoid cavity.

* * * * *